United States Patent
Kwan et al.

(10) Patent No.: US 10,617,693 B2
(45) Date of Patent: Apr. 14, 2020

(54) METHODS OF TREATING AND/OR PREVENTING ACTINIC KERATOSIS

(71) Applicant: Athenex, Inc., Buffalo, NY (US)

(72) Inventors: Min-Fun Rudolf Kwan, Summit, NJ (US); Johnson Yiu-Nam Lau, Newport Beach, CA (US); E. Douglas Kramer, Stamford, CT (US); David Lawrence Cutler, Moorestown, NJ (US); Jane Fang, Newport Beach, CA (US)

(73) Assignee: Athenex, Inc., Buffalo, NY (US)

( * ) Notice: Subject to any disclaimer, the term of this patent is extended or adjusted under 35 U.S.C. 154(b) by 0 days.

(21) Appl. No.: 15/918,100

(22) Filed: Mar. 12, 2018

(65) Prior Publication Data
US 2018/0256589 A1  Sep. 13, 2018

Related U.S. Application Data

(60) Provisional application No. 62/469,889, filed on Mar. 10, 2017.

(51) Int. Cl.
*A61K 31/5377* (2006.01)
*A61P 17/00* (2006.01)
*A61K 9/00* (2006.01)

(52) U.S. Cl.
CPC ........ *A61K 31/5377* (2013.01); *A61K 9/0014* (2013.01); *A61P 17/00* (2018.01)

(58) Field of Classification Search
None
See application file for complete search history.

(56) References Cited

U.S. PATENT DOCUMENTS

| | | |
|---|---|---|
| 7,300,931 B2 | 11/2007 | Hangauer |
| 7,538,252 B2 | 5/2009 | Ossovskaya et al. |
| 7,851,470 B2 | 12/2010 | Hangauer |
| 7,935,697 B2 | 5/2011 | Hangauer |
| 7,939,529 B2 | 5/2011 | Hangauer |
| 7,968,574 B2 | 6/2011 | Hangauer |
| 8,003,641 B2 | 8/2011 | Hangauer |
| 8,236,799 B2 | 8/2012 | Hangauer |
| 8,293,739 B2 | 10/2012 | Hangauer et al. |
| 8,309,549 B2 | 11/2012 | Hangauer |
| 8,598,169 B2 | 2/2013 | Hangauer |
| 8,901,297 B2 | 12/2014 | Hangauer et al. |
| 8,980,890 B2 | 3/2015 | Hangauer, Jr. |
| 9,556,120 B2 | 1/2017 | Hangauer et al. |
| 9,580,387 B2 | 2/2017 | Hangauer |
| 9,655,903 B2 | 5/2017 | Hangauer |
| 2010/0249130 A1 | 9/2010 | Hangauer |
| 2013/0197089 A1 | 8/2013 | Warnecke |
| 2014/0256667 A1 | 9/2014 | Moy |
| 2017/0101378 A1 | 4/2017 | Hangauer et al. |
| 2017/0196874 A1 | 7/2017 | Hangauer |

FOREIGN PATENT DOCUMENTS

| | | |
|---|---|---|
| WO | WO 2008/082637 A1 | 7/2008 |
| WO | WO 2008/144045 A1 | 11/2008 |
| WO | WO 2010/135429 A2 | 11/2010 |

OTHER PUBLICATIONS

Mayo Clinic, "Actinic keratosis", "www.mayoclinic.org/diseases-conditions/actinic-keratosis/symptoms-causes/syc-20354969", Mar. 7, 2018, 3 pages; downloaded Jun. 23, 2018.*
Kinex receives FDA approval to begin Phase I study of KX2-391 ointment for actinic keratosis' 2014, 2 pages. Retrieved from Internet: (URL: https://www.news-medical.net/news/20140725/Kinex-receives-FDA-approval-to-begin-Phase-I-study-of-KX2-391-Ointment-for-actinic-keratosis.aspx).
Gail M. et al., "Dose Finding in Drug Development", *Statistics for Biology and Health,* Springer Science+Business Media, Inc., 2006, Preface, and Chapter I.
Savary, J. et. al. "The right dose in the right place: an overview of current prescription instruction and application modalities for topical psoriasis treatments", *JEADV,* 2005, 19, 14-17.

* cited by examiner

*Primary Examiner* — Savitha M Rao
*Assistant Examiner* — Gregg Polansky
(74) *Attorney, Agent, or Firm* — Cooley LLP; Heidi A. Erlacher; Chen Chen

(57) ABSTRACT

The application pertains to methods of treating and/or preventing actinic keratosis, comprising administering a therapeutically effective amount of KX-01,

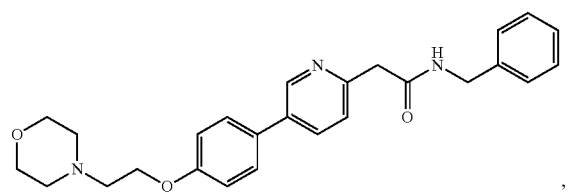

to a subject in need thereof.

25 Claims, 4 Drawing Sheets

Adverse skin reaction example from current treatments

Skin reaction from KX-01 treatment

Adverse skin reaction example from current treatments

Skin reaction from KX-01 treatment

METHODS OF TREATING AND/OR PREVENTING ACTINIC KERATOSIS

RELATED APPLICATION

This application claims priority to, and the benefit of U.S. Provisional Application No. 62/469,889, filed on Mar. 10, 2017, the entire contents of which are incorporated herein by reference.

BACKGROUND

Actinic keratosis, or solar keratosis, are scaly, crusty growths (lesions) caused by damage from the sun's ultraviolet rays. They typically appear on sun-exposed areas such as the face, bald scalp, lips, and the back of the hands, and are often elevated, rough in texture, and resemble warts. Most become red, but some will be tan, pink, and/or flesh-toned. If left untreated, up to ten percent of actinic keratosis develop into squamous cell carcinoma (SCC), the second most common form of skin cancer. In rarer instances, actinic keratosis may also turn into basal cell carcinomas, the most common form of skin cancer. It is estimated that more than 58 million Americans suffers from actinic keratosis. The treatments for actinic keratosis include cryotherapy, surgical removal, chemical peel, photodynamic therapy, laser resurfacing, and/or drug-containing gel and creams. Due to the prevalence of actinic keratosis, and its ability to turn into skin cancer if not treated properly, development of further treatments is warranted.

SUMMARY

In one aspect, this application pertains at least in part, to a method of treating and/or preventing actinic keratosis, comprising administering to a subject in need thereof a therapeutically effective amount of KX-01:

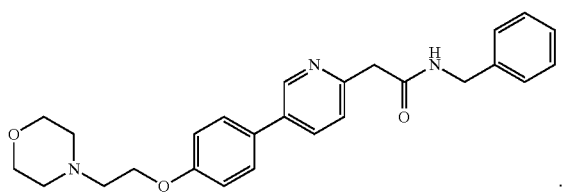 [SMILES: O=C(Cc1ccc(-c2ccc(OCCN3CCOCC3)cc2)cn1)NCc1ccccc1]

In one aspect, KX-01 is administered to an affected area of the subject at a dose from about 0.1 mg to about 10 mg.

In one aspect, KX-01 is administered to an affected area of the subject at a dose from about 0.2 mg to about 5 mg.

In one aspect, KX-01 is administered to an affected area of the subject at a dose from about 0.5 mg to about 2.5 mg.

In one aspect, KX-01 is administered to an affected area of the subject at a dose of about 0.2 mg, about 0.3 mg, about 0.4 mg, about 0.5 mg, about 0.6 mg, about 0.7 mg, about 0.8 mg, about 0.9 mg, about 1 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3 mg, about 4 mg, or about 5 mg.

In one aspect, KX-01 is administered to an affected area of the subject at a dose of about 0.5 mg, about 0.6 mg, about 0.7 mg, about 0.8 mg, about 0.9 mg, about 1 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, or about 2.5 mg.

In one aspect, KX-01 is administered to an affected area of the subject at a dose from about 0.0003 $mg/cm^2$ to about 10 $mg/cm^2$.

In one aspect, KX-01 is administered to an affected area of the subject at a dose from about 0.001 $mg/cm^2$ to about 0.4 $mg/cm^2$.

In one aspect, KX-01 is administered to an affected area of the subject at a dose from about 0.005 $mg/cm^2$ to about 0.1 $mg/cm^2$ In one aspect, KX-01 is administered to an affected area of the subject at a dose from about 0.005 $mg/cm^2$ to about 0.02 $mg/cm^2$.

In one aspect, KX-01 is administered to an affected area of the subject at a dose from about 0.025 $mg/cm^2$ to about 0.1 $mg/cm^2$.

In one aspect, KX-01 is administered to an affected area of the subject at a dose of about 0.001 $mg/cm^2$, about 0.002 $mg/cm^2$, about 0.003 $mg/cm^2$, about 0.004 $mg/cm^2$, about 0.005 $mg/cm^2$, about 0.006 $mg/cm^2$, about 0.007 $mg/cm^2$, about 0.008 $mg/cm^2$, about 0.009 $mg/cm^2$, about 0.01 $mg/cm^2$, about 0.02 $mg/cm^2$, about 0.03 $mg/cm^2$, about 0.04 $mg/cm^2$, about 0.05 $mg/cm^2$, about 0.06 $mg/cm^2$, about 0.07 $mg/cm^2$, about 0.08 $mg/cm^2$, about 0.09 $mg/cm^2$, about 0.1 $mg/cm^2$, about 0.15 $mg/cm^2$, about 0.2 $mg/cm^2$, about 0.25 $mg/cm^2$, about 0.3 $mg/cm^2$, about 0.35 $mg/cm^2$, or about 0.4 $mg/cm^2$.

In one aspect, KX-01 is administered to an affected area of the subject at a dose of about 0.005 $mg/cm^2$, about 0.006 $mg/cm^2$, about 0.007 $mg/cm^2$, about 0.008 $mg/cm^2$, about 0.009 $mg/cm^2$, about 0.01 $mg/cm^2$, about 0.015 $mg/cm^2$, about 0.02 $mg/cm^2$, about 0.025 $mg/cm^2$, about 0.03 $mg/cm^2$, about 0.035 $mg/cm^2$, about 0.04 $mg/cm^2$, about 0.045 $mg/cm^2$, about 0.05 $mg/cm^2$, about 0.055 $mg/cm^2$, about 0.06 $mg/cm^2$, about 0.065 $mg/cm^2$, about 0.07 $mg/cm^2$, about 0.075 $mg/cm^2$, about 0.08 $mg/cm^2$, about 0.085 $mg/cm^2$, about 0.09 $mg/cm^2$, about 0.095 $mg/cm^2$, or about 0.1 $mg/cm^2$.

In one aspect, the affected area of the subject is about 0.01 $cm^2$ to about 300 $cm^2$.

In one aspect, the affected area of the subject is about 1 $cm^2$ to about 200 $cm^2$, about 1 $cm^2$ to about 100 $cm^2$, about 1 $cm^2$ to about 75 $cm^2$, about 1 $cm^2$ to about 50 $cm^2$, or about 1 $cm^2$ to about 25 $cm^2$.

In one aspect, the affected area of the subject is about 10 $cm^2$ to about 200 $cm^2$, about 10 $cm^2$ to about 100 $cm^2$, about 10 $cm^2$ to about 75 $cm^2$, about 10 $cm^2$ to about 50 $cm^2$, or about 10 $cm^2$ to about 25 $cm^2$.

In one aspect, the affected area of the subject is about 25 $cm^2$ to about 200 $cm^2$, about 25 $cm^2$ to about 100 $cm^2$, about 25 $cm^2$ to about 75 $cm^2$, or about 25 $cm^2$ to about 50 $cm^2$.

In one aspect, the affected area of the subject is about 25 $cm^2$ to about 100 $cm^2$, about 25 $cm^2$ to about 90 $cm^2$, about 25 $cm^2$ to about 80 $cm^2$, or about 25 $cm^2$ to about 70 $cm^2$, about 25 $cm^2$ to about 60 $cm^2$, about 25 $cm^2$ to about 50 $cm^2$, about 25 $cm^2$ to about 40 $cm^2$, or about 25 $cm^2$ to about 30 $cm^2$.

In one aspect, the affected area of the subject is about 25 $cm^2$, about 30 $cm^2$, about 35 $cm^2$, about 40 $cm^2$, about 45 $cm^2$, about 50 $cm^2$, about 55 $cm^2$, about 60 $cm^2$, about 65 $cm^2$, about 70 $cm^2$, about 75 $cm^2$, about 80 $cm^2$, about 85 $cm^2$, about 90 $cm^2$, about 95 $cm^2$, or about 100 $cm^2$.

In one aspect, the affected area of the subject is the skin.

In one aspect, the affected area of the subject is located at one or more locations independently selected from the scalp, forehead, forearm, face, nose, ears, eye lids, lips, neck, arms, hands, trunk, legs, and feet.

In one aspect, the subject has more than one affected area.

In one aspect, KX-01 is administered once a week, once every three days, once every two days, once a day, twice a day, three times a day, or four times a day.

In one aspect, KX-01 is administered once a day or twice a day.

In one aspect, KX-01 is administered once a day.

In one aspect, KX-01 is administered for 1, 2, 3, 4, 5, 6, 7, 8, 9, 10, 11, 12, 13, 14, 15, 16, 17, 18, 19, 20 or 21 days.

In one aspect, KX-01 is administered for 1, 2, 3, 4, 5, 6, 7, 8, 9, 10, 11, 12, 13, or 14 days.

In one aspect, KX-01 is administered for 1, 2, 3, 4, 5, 6, or 7 days.

In one aspect, KX-01 is administered for 1, 2, 3, 4 or 5 days.

In one aspect, KX-01 is administered for 1, 2, 3, 4, 5, or 6 days per week.

In one aspect, KX-01 is administered for 2, 3, 4, 5, or 6 days per week.

In one aspect, KX-01 is administered once or twice daily continuously for more than one day per week, followed by discontinuation of the administration for the rest of the week.

In one aspect, KX-01 is administered once or twice daily every other day.

In one aspect, KX-01 is administered once or twice daily every three days, every four days, every five days, every six days, or every seven days.

In one aspect, KX-01 is administered once or twice daily for two days in a row every three days, every four days, every five days, every six days, or every seven days.

In one aspect, KX-01 is administered once or twice daily for three days in a row every four days, every five days, every six days, or every seven days.

In one aspect, KX-01 is administered once or twice daily for four days in a row every five days, every six days, or every seven days.

In one aspect, KX-01 is administered until the actinic keratosis is fully treated.

In one aspect, KX-01 is administered topically.

In one aspect, the administration of KX-01 reduces the number and/or severity of local skin reactions or other adverse side effects in the subject compared to other treatments of actinic keratosis.

In one aspect, the administration of KX-01 reduces the number of the subjects that have local skin reactions or other adverse side effects compared to other treatments of actinic keratosis.

In one aspect, the local skin reaction is selected from the group selected from vesiculation, postulation, erosion, ulceration, redness, swelling, flaking, scaling, hard lumps, dryness, pus, and blistering.

In one aspect, the other side effect is selected from the group consisting of application site pain, application site pruritus, application site irritation, application site swelling, application site burning sensation, application site infection, periorbital edema, nasopharyngitis, chills, sore throat, drooping eyes, puffy eyes, hypopigmentation, hyperpigmentation, and headache.

In one aspect, this application pertains at least in part, to KX-01 for use (e.g., topical use) in the treatment and/or prevention of actinic keratosis. In certain aspects, KX-01 is for use at the doses, dosing schedules, and/or one or more affected area in a subject in need thereof as described herein.

In one aspect, this application pertains at least in part, to use (e.g., topical use) of KX-01 in the treatment and/or prevention of actinic keratosis. In certain aspects, KX-01 is used at the doses, dosing schedules, and/or one or more affected area in a subject in need thereof as described herein.

In one aspect, this application pertains at least in part, to use of KX-01 in the manufacture of a medicament for the treatment and/or prevention of actinic keratosis. In certain aspects, KX-01 is used at the doses, dosing schedules, and/or one or more affected area in a subject in need thereof as described herein.

DETAILED DESCRIPTION

Figure 1:
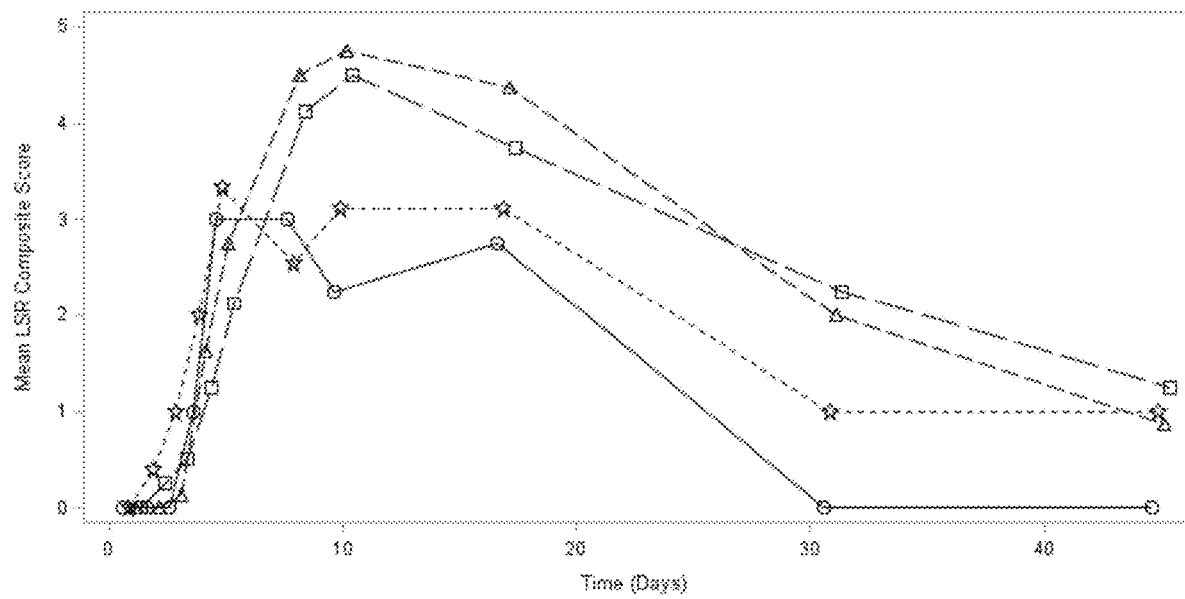
FIG. 1. Mean LSR composite scores vs. time—Phase 1 study of KX-01 administered topically on the dorsal forearm. ○ Cohort 1 (N=4): 0.5 mg KX-01 topically administered to a 25 cm² area with 4-8 typical AK lesions, daily for 3 consecutive days. ☆ Cohort 2 (N=10): 2.0 mg KX-01 topically administered to a 100 cm² area with 8-16 typical AK lesions, daily for 3 consecutive days. Δ Cohort 3 (N=8): 0.5 mg KX-01 topically administered to a 25 cm² area with 4-8 typical AK lesions, daily for 5 consecutive days. □ Cohort 4 (N=8): 2.0 mg KX-01 topically administered to a 100 cm² area with 8-16 typical AK lesions, daily for 5 consecutive days.

The application pertains, at least in part, to a method of treating and/or preventing actinic keratosis, comprising administering to a subject in need thereof a therapeutically effective amount of KX-01:

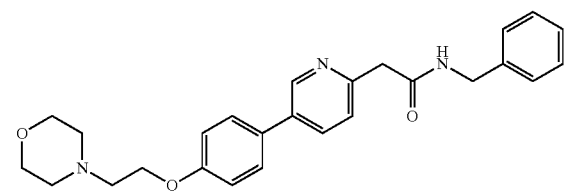

The application pertains, at least in part, to a method of treating actinic keratosis comprising administering to a subject in need thereof a therapeutically effective amount of KX-01:

The application pertains, at least in part, to a method of preventing actinic keratosis comprising administering to a subject in need thereof a therapeutically effective amount of KX-01:

In one embodiment, for any of the methods disclosed in this application, KX-01 is administered to an affected area of the subject at a dose from about 0.1 mg to about 10 mg.

In one embodiment, for any of the methods disclosed in this application, KX-01 is administered to an affected area of the subject at a dose from about 0.2 mg to about 5 mg.

In one embodiment, for any of the methods disclosed in this application, KX-01 is administered to an affected area of the subject at a dose from about 0.5 mg to about 2.5 mg.

In one embodiment, for any of the methods disclosed in this application, KX-01 is administered to an affected area of the subject at a dose from about 0.1 mg to about 9 mg, from about 0.1 mg to about 8 mg, from about 0.1 mg to about 7 mg, from about 0.1 mg to about 6 mg, from about 0.1 mg to about 5 mg, from about 0.1 mg to about 4 mg, from about 0.1 mg to about 3 mg, from about 0.1 mg to about 2 mg, from about 0.1 mg to about 1 mg, from about 0.1 mg to about 0.9 mg, from about 0.1 mg to about 0.8 mg, from about 0.1 mg to about 0.7 mg, from about 0.1 mg to about 0.6 mg, from about 0.1 mg to about 0.5 mg, from about 0.1 mg to about 0.4 mg, from about 0.1 mg to about 0.3 mg, or from about 0.1 mg to about 0.2 mg.

In one embodiment, for any of the methods disclosed in this application, KX-01 is administered to an affected area of the subject at a dose from about 0.2 mg to about 10 mg, from about 0.2 mg to about 9 mg, from about 0.2 mg to about 8 mg, from about 0.2 mg to about 7 mg, from about 0.2 mg to about 6 mg, from about 0.2 mg to about 5 mg, from about 0.2 mg to about 4 mg, from about 0.2 mg to about 3 mg, from about 0.2 mg to about 2 mg, from about 0.2 mg to about 1 mg, from about 0.2 mg to about 0.9 mg, from about 0.2 mg to about 0.8 mg, from about 0.2 mg to about 0.7 mg, from about 0.2 mg to about 0.6 mg, from about 0.2 mg to about 0.5 mg, from about 0.2 mg to about 0.4 mg, or from about 0.2 mg to about 0.3 mg, In one embodiment, for any of the methods disclosed in this application, KX-01 is administered to an affected area of the subject at a dose from about 0.3 mg to about 10 mg, from about 0.3 mg to about 9 mg, from about 0.3 mg to about 8 mg, from about 0.3 mg to about 7 mg, from about 0.3 mg to about 6 mg, from about 0.3 mg to about 5 mg, from about 0.3 mg to about 4 mg, from about 0.3 mg to about 3 mg, from about 0.3 mg to about 2 mg, from about 0.3 mg to about 1 mg, from about 0.3 mg to about 0.9 mg, from about 0.3 mg to about 0.8 mg, from about 0.3 mg to about 0.7 mg, from about 0.3 mg to about 0.6 mg, from about 0.3 mg to about 0.5 mg, or from about 0.3 mg to about 0.4 mg.

In one embodiment, for any of the methods disclosed in this application, KX-01 is administered to an affected area of the subject at a dose from about 0.4 mg to about 10 mg, from about 0.4 mg to about 9 mg, from about 0.4 mg to about 8 mg, from about 0.4 mg to about 7 mg, from about 0.4 mg to about 6 mg, from about 0.4 mg to about 5 mg, from about 0.4 mg to about 4 mg, from about 0.4 mg to about 3 mg, from about 0.4 mg to about 2 mg, from about 0.4 mg to about 1 mg, from about 0.4 mg to about 0.9 mg, from about 0.4 mg to about 0.8 mg, from about 0.4 mg to about 0.7 mg, from about 0.4 mg to about 0.6 mg, or from about 0.4 mg to about 0.5 mg.

In one embodiment, for any of the methods disclosed in this application, KX-01 is administered to an affected area of the subject at a dose from about 0.5 mg to about 10 mg, from about 0.5 mg to about 9 mg, from about 0.5 mg to about 8 mg, from about 0.5 mg to about 7 mg, from about 0.5 mg to about 6 mg, from about 0.5 mg to about 5 mg, from about 0.5 mg to about 4 mg, from about 0.5 mg to about 3 mg, from about 0.5 mg to about 2 mg, from about 0.5 mg to about 1 mg, from about 0.5 mg to about 0.9 mg, from about 0.5 mg to about 0.8 mg, from about 0.5 mg to about 0.7 mg, or from about 0.5 mg to about 0.6 mg.

In one embodiment, for any of the methods disclosed in this application, KX-01 is administered to an affected area of the subject at a dose from about 0.6 mg to about 10 mg, from about 0.6 mg to about 9 mg, from about 0.6 mg to about 8 mg, from about 0.6 mg to about 7 mg, from about 0.6 mg to about 6 mg, from about 0.6 mg to about 5 mg, from about 0.6 mg to about 4 mg, from about 0.6 mg to about 3 mg, from about 0.6 mg to about 2 mg, from about 0.6 mg to about 1 mg, from about 0.6 mg to about 0.9 mg, from about 0.6 mg to about 0.8 mg, or from about 0.6 mg to about 0.7 mg.

In one embodiment, for any of the methods disclosed in this application, KX-01 is administered to an affected area of the subject at a dose from about 0.7 mg to about 10 mg, from about 0.7 mg to about 9 mg, from about 0.7 mg to about 8 mg, from about 0.7 mg to about 7 mg, from about 0.7 mg to about 6 mg, from about 0.7 mg to about 5 mg, from about 0.7 mg to about 4 mg, from about 0.7 mg to about 3 mg, from about 0.7 mg to about 2 mg, from about 0.7 mg to about 1 mg, from about 0.7 mg to about 0.9 mg, or from about 0.7 mg to about 0.8 mg.

In one embodiment, for any of the methods disclosed in this application, KX-01 is administered to an affected area of the subject at a dose from about 0.8 mg to about 10 mg, from about 0.8 mg to about 9 mg, from about 0.8 mg to about 8 mg, from about 0.8 mg to about 7 mg, from about 0.8 mg to about 6 mg, from about 0.8 mg to about 5 mg, from about 0.8 mg to about 4 mg, from about 0.8 mg to about 3 mg, from about 0.8 mg to about 2 mg, from about 0.8 mg to about 1 mg, or from about 0.8 mg to about 0.9 mg.

In one embodiment, for any of the methods disclosed in this application, KX-01 is administered to an affected area of the subject at a dose from about 0.9 mg to about 10 mg, from about 0.9 mg to about 9 mg, from about 0.9 mg to about 8 mg, from about 0.9 mg to about 7 mg, from about 0.9 mg to about 6 mg, from about 0.9 mg to about 5 mg, from about 0.9 mg to about 4 mg, from about 0.9 mg to about 3 mg, from about 0.9 mg to about 2 mg, or from about 0.9 mg to about 1 mg.

In one embodiment, for any of the methods disclosed in this application, KX-01 is administered to an affected area of the subject at a dose from about 1 mg to about 10 mg, from about 1 mg to about 9 mg, from about 1 mg to about 8 mg, from about 1 mg to about 7 mg, from about 1 mg to about 6 mg, from about 1 mg to about 5 mg, from about 1 mg to about 4 mg, from about 1 mg to about 3 mg, or from about 1 mg to about 2 mg.

In one embodiment, for any of the methods disclosed in this application, KX-01 is administered to an affected area of the subject at a dose from about 2 mg to about 10 mg, from about 2 mg to about 9 mg, from about 2 mg to about 8 mg, from about 2 mg to about 7 mg, from about 2 mg to about 6 mg, from about 2 mg to about 5 mg, from about 2 mg to about 4 mg, or from about 2 mg to about 3 mg.

In one embodiment, for any of the methods disclosed in this application, KX-01 is administered to an affected area of the subject at a dose from about 0.2 mg to about 10 mg, from about 0.3 mg to about 10 mg, from about 0.4 mg to about 10 mg, from about 0.5 mg to about 10 mg, from about 0.6 mg to about 10 mg, from about 0.7 mg to about 10 mg, from about 0.8 mg to about 10 mg, from about 0.9 mg to about 10 mg, from about 1 mg to about 10 mg, from about 2 mg to about 10 mg, from about 3 mg to about 10 mg, from about 4 mg to about 10 mg, from about 5 mg to about 10 mg, from about 6 mg to about 10 mg, from about 7 mg to about 10 mg, from about 8 mg to about 10 mg, or from about 9 mg to about 10 mg.

In one embodiment, for any of the methods disclosed in this application, KX-01 is administered to an affected area of the subject at a dose from about 0.1 mg to about 9 mg, from about 0.2 mg to about 9 mg, from about 0.3 mg to about 9 mg, from about 0.4 mg to about 9 mg, from about 0.5 mg to about 9 mg, from about 0.6 mg to about 9 mg, from about 0.7 mg to about 9 mg, from about 0.8 mg to about 9 mg, from about 0.9 mg to about 9 mg, from about 1 mg to about 9 mg, from about 2 mg to about 9 mg, from about 3 mg to about 9 mg, from about 4 mg to about 9 mg, from about 5 mg to about 9 mg, from about 6 mg to about 9 mg, from about 7 mg to about 9 mg, or from about 8 mg to about 9 mg.

In one embodiment, for any of the methods disclosed in this application, KX-01 is administered to an affected area of the subject at a dose from about 0.1 mg to about 8 mg, from about 0.2 mg to about 8 mg, from about 0.3 mg to about 8 mg, from about 0.4 mg to about 8 mg, from about 0.5 mg to about 8 mg, from about 0.6 mg to about 8 mg, from about 0.7 mg to about 8 mg, from about 0.8 mg to about 8 mg, from about 0.9 mg to about 8 mg, from about 1 mg to about 8 mg, from about 2 mg to about 8 mg, from about 3 mg to about 8 mg, from about 4 mg to about 8 mg, from about 5 mg to about 8 mg, from about 6 mg to about 8 mg, or from about 7 mg to about 8 mg.

In one embodiment, for any of the methods disclosed in this application, KX-01 is administered to an affected area of the subject at a dose from about 0.1 mg to about 7 mg, from about 0.2 mg to about 7 mg, from about 0.3 mg to about 7 mg, from about 0.4 mg to about 7 mg, from about 0.5 mg to about 7 mg, from about 0.6 mg to about 7 mg, from about 0.7 mg to about 7 mg, from about 0.8 mg to about 7 mg, from about 0.9 mg to about 7 mg, from about 1 mg to about 7 mg, from about 2 mg to about 7 mg, from about 3 mg to about 7 mg, from about 4 mg to about 7 mg, from about 5 mg to about 7 mg, or from about 6 mg to about 7 mg.

In one embodiment, for any of the methods disclosed in this application, KX-01 is administered to an affected area of the subject at a dose from about 0.1 mg to about 6 mg, from about 0.2 mg to about 6 mg, from about 0.3 mg to about 6 mg, from about 0.4 mg to about 6 mg, from about 0.5 mg to about 6 mg, from about 0.6 mg to about 6 mg, from about 0.7 mg to about 6 mg, from about 0.8 mg to about 6 mg, from about 0.9 mg to about 6 mg, from about 1 mg to about 6 mg, from about 2 mg to about 6 mg, from about 3 mg to about 6 mg, from about 4 mg to about 6 mg, or from about 5 mg to about 6 mg.

In one embodiment, for any of the methods disclosed in this application, KX-01 is administered to an affected area of the subject at a dose from about 0.1 mg to about 5 mg, from about 0.2 mg to about 5 mg, from about 0.3 mg to about 5 mg, from about 0.4 mg to about 5 mg, from about 0.5 mg to about 5 mg, from about 0.6 mg to about 5 mg, from about 0.7 mg to about 5 mg, from about 0.8 mg to about 5 mg, from about 0.9 mg to about 5 mg, from about 1 mg to about 5 mg, from about 2 mg to about 5 mg, from about 3 mg to about 5 mg, or from about 4 mg to about 5 mg.

In one embodiment, for any of the methods disclosed in this application, KX-01 is administered to an affected area of the subject at a dose from about 0.1 mg to about 4 mg, from about 0.2 mg to about 4 mg, from about 0.3 mg to about 4 mg, from about 0.4 mg to about 4 mg, from about 0.5 mg to about 4 mg, from about 0.6 mg to about 4 mg, from about 0.7 mg to about 4 mg, from about 0.8 mg to about 4 mg, from about 0.9 mg to about 4 mg, from about 1 mg to about 4 mg, from about 2 mg to about 4 mg, or from about 3 mg to about 4 mg.

In one embodiment, for any of the methods disclosed in this application, KX-01 is administered to an affected area of the subject at a dose from about 0.1 mg to about 3 mg, from about 0.2 mg to about 3 mg, from about 0.3 mg to about 3 mg, from about 0.4 mg to about 3 mg, from about 0.5 mg to about 3 mg, from about 0.6 mg to about 3 mg, from about 0.7 mg to about 3 mg, from about 0.8 mg to about 3 mg, from about 0.9 mg to about 3 mg, from about 1 mg to about 3 mg, or from about 2 mg to about 3 mg.

In one embodiment, for any of the methods disclosed in this application, KX-01 is administered to an affected area of the subject at a dose from about 0.1 mg to about 2 mg, from about 0.2 mg to about 2 mg, from about 0.3 mg to about 2 mg, from about 0.4 mg to about 2 mg, from about 0.5 mg to about 2 mg, from about 0.6 mg to about 2 mg, from about 0.7 mg to about 2 mg, from about 0.8 mg to about 2 mg, from about 0.9 mg to about 2 mg, or from about 1 mg to about 2 mg.

In one embodiment, for any of the methods disclosed in this application, KX-01 is administered to an affected area of the subject at a dose from about 0.1 mg to about 1 mg, from about 0.2 mg to about 1 mg, from about 0.3 mg to about 1 mg, from about 0.4 mg to about 1 mg, from about 0.5 mg to about 1 mg, from about 0.6 mg to about 1 mg, from about 0.7 mg to about 1 mg, from about 0.8 mg to about 1 mg, or from about 0.9 mg to about 1 mg.

In one embodiment, for any of the methods disclosed in this application, KX-01 is administered to an affected area of the subject at a dose from about 0.2 mg to about 3 mg, from about 0.2 mg to about 2.9 mg, from about 0.2 mg to about 2.8 mg, from about 0.2 mg to about 2.7 mg, from about 0.2 mg to about 2.6 mg, from about 0.2 mg to about 2.5 mg, from about 0.2 mg to about 2.4 mg, from about 0.2 mg to about 2.3 mg, from about 0.2 mg to about 2.2 mg, from about 0.2 mg to about 2.1 mg, or from about 0.2 mg to about 2.0 mg.

In one embodiment, for any of the methods disclosed in this application, KX-01 is administered to an affected area of the subject at a dose from about 0.3 mg to about 3 mg, from about 0.3 mg to about 2.9 mg, from about 0.3 mg to about 2.8 mg, from about 0.3 mg to about 2.7 mg, from about 0.3 mg to about 2.6 mg, from about 0.3 mg to about 2.5 mg, from about 0.3 mg to about 2.4 mg, from about 0.3 mg to about 2.3 mg, from about 0.3 mg to about 2.2 mg, from about 0.3 mg to about 2.1 mg, or from about 0.3 mg to about 2.0 mg.

In one embodiment, for any of the methods disclosed in this application, KX-01 is administered to an affected area of the subject at a dose from about 0.4 mg to about 3 mg, from about 0.4 mg to about 2.9 mg, from about 0.4 mg to about 2.8 mg, from about 0.4 mg to about 2.7 mg, from about 0.4 mg to about 2.6 mg, from about 0.4 mg to about 2.5 mg, from about 0.4 mg to about 2.4 mg, from about 0.4 mg to about 2.3 mg, from about 0.4 mg to about 2.2 mg, from about 0.4 mg to about 2.1 mg, or from about 0.4 mg to about 2.0 mg.

In one embodiment, for any of the methods disclosed in this application, KX-01 is administered to an affected area of the subject at a dose from about 0.5 mg to about 3 mg, from about 0.5 mg to about 2.9 mg, from about 0.5 mg to about 2.8 mg, from about 0.5 mg to about 2.7 mg, from about 0.5 mg to about 2.6 mg, from about 0.5 mg to about 2.5 mg, from about 0.5 mg to about 2.4 mg, from about 0.5 mg to about 2.3 mg, from about 0.5 mg to about 2.2 mg, from about 0.5 mg to about 2.1 mg, or from about 0.5 mg to about 2.0 mg.

In one embodiment, for any of the methods disclosed in this application, KX-01 is administered to an affected area of the subject at a dose from about 0.2 mg to about 3 mg, from about 0.3 mg to about 3 mg, from about 0.4 mg to about 3 mg, from about 0.5 mg to about 3 mg, from about 0.6 mg to about 3 mg, from about 0.7 mg to about 3 mg, from about 0.8 mg to about 3 mg, from about 0.9 mg to about 3 mg, or from about 1 mg to about 3 mg.

In one embodiment, for any of the methods disclosed in this application, KX-01 is administered to an affected area of the subject at a dose from about 0.2 mg to about 2.9 mg, from about 0.3 mg to about 2.9 mg, from about 0.4 mg to about 2.9 mg, from about 0.5 mg to about 2.9 mg, from about 0.6 mg to about 2.9 mg, from about 0.7 mg to about 2.9 mg, from about 0.8 mg to about 2.9 mg, from about 0.9 mg to about 2.9 mg, or from about 1 mg to about 2.9 mg.

In one embodiment, for any of the methods disclosed in this application, KX-01 is administered to an affected area of the subject at a dose from about 0.2 mg to about 2.8 mg, from about 0.3 mg to about 2.8 mg, from about 0.4 mg to about 2.8 mg, from about 0.5 mg to about 2.8 mg, from about 0.6 mg to about 2.8 mg, from about 0.7 mg to about 2.8 mg, from about 0.8 mg to about 2.8 mg, from about 0.9 mg to about 2.8 mg, or from about 1 mg to about 2.8 mg.

In one embodiment, for any of the methods disclosed in this application, KX-01 is administered to an affected area of the subject at a dose from about 0.2 mg to about 2.7 mg, from about 0.3 mg to about 2.7 mg, from about 0.4 mg to about 2.7 mg, from about 0.5 mg to about 2.7 mg, from about 0.6 mg to about 2.7 mg, from about 0.7 mg to about 2.7 mg, from about 0.8 mg to about 2.7 mg, from about 0.9 mg to about 2.7 mg, or from about 1 mg to about 2.7 mg.

In one embodiment, for any of the methods disclosed in this application, KX-01 is administered to an affected area of the subject at a dose from about 0.2 mg to about 2.6 mg, from about 0.3 mg to about 2.6 mg, from about 0.4 mg to about 2.6 mg, from about 0.5 mg to about 2.6 mg, from about 0.6 mg to about 2.6 mg, from about 0.7 mg to about 2.6 mg, from about 0.8 mg to about 2.6 mg, from about 0.9 mg to about 2.6 mg, or from about 1 mg to about 2.6 mg.

In one embodiment, for any of the methods disclosed in this application, KX-01 is administered to an affected area of the subject at a dose from about 0.2 mg to about 2.5 mg, from about 0.3 mg to about 2.5 mg, from about 0.4 mg to about 2.5 mg, from about 0.5 mg to about 2.5 mg, from about 0.6 mg to about 2.5 mg, from about 0.7 mg to about 2.5 mg, from about 0.8 mg to about 2.5 mg, from about 0.9 mg to about 2.5 mg, or from about 1 mg to about 2.5 mg.

In one embodiment, for any of the methods disclosed in this application, KX-01 is administered to an affected area of the subject at a dose from about 0.2 mg to about 2.4 mg, from about 0.3 mg to about 2.4 mg, from about 0.4 mg to about 2.4 mg, from about 0.5 mg to about 2.4 mg, from about 0.6 mg to about 2.4 mg, from about 0.7 mg to about 2.4 mg, from about 0.8 mg to about 2.4 mg, from about 0.9 mg to about 2.4 mg, or from about 1 mg to about 2.4 mg.

In one embodiment, for any of the methods disclosed in this application, KX-01 is administered to an affected area of the subject at a dose from about 0.2 mg to about 2.3 mg, from about 0.3 mg to about 2.3 mg, from about 0.4 mg to about 2.3 mg, from about 0.5 mg to about 2.3 mg, from about 0.6 mg to about 2.3 mg, from about 0.7 mg to about 2.3 mg, from about 0.8 mg to about 2.3 mg, from about 0.9 mg to about 2.3 mg, or from about 1 mg to about 2.3 mg.

In one embodiment, for any of the methods disclosed in this application, KX-01 is administered to an affected area of the subject at a dose from about 0.2 mg to about 2.2 mg, from about 0.3 mg to about 2.2 mg, from about 0.4 mg to about 2.2 mg, from about 0.5 mg to about 2.2 mg, from about 0.6 mg to about 2.2 mg, from about 0.7 mg to about 2.2 mg, from about 0.8 mg to about 2.2 mg, from about 0.9 mg to about 2.2 mg, or from about 1 mg to about 2.2 mg.

In one embodiment, for any of the methods disclosed in this application, KX-01 is administered to an affected area of the subject at a dose from about 0.2 mg to about 2.1 mg, from about 0.3 mg to about 2.1 mg, from about 0.4 mg to about 2.1 mg, from about 0.5 mg to about 2.1 mg, from about 0.6 mg to about 2.1 mg, from about 0.7 mg to about 2.1 mg, from about 0.8 mg to about 2.1 mg, from about 0.9 mg to about 2.1 mg, or from about 1 mg to about 2.1 mg.

In one embodiment, for any of the methods disclosed in this application, KX-01 is administered to an affected area of the subject at a dose from about 0.2 mg to about 2 mg, from about 0.3 mg to about 2 mg, from about 0.4 mg to about 2 mg, from about 0.5 mg to about 2 mg, from about 0.6 mg to about 2 mg, from about 0.7 mg to about 2 mg, from about 0.8 mg to about 2 mg, from about 0.9 mg to about 2 mg, or from about 1 mg to about 2 mg.

In one embodiment, for any of the methods disclosed in this application, KX-01 is administered to an affected area of the subject at a dose of about 0.2 mg, about 0.3 mg, about 0.4 mg, about 0.5 mg, about 0.6 mg, about 0.7 mg, about 0.8 mg, about 0.9 mg, about 1 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3 mg, about 4 mg, or about 5 mg.

In one embodiment, for any of the methods disclosed in this application, KX-01 is administered to an affected area of the subject at a dose of about 0.2 mg, about 0.3 mg, about 0.4 mg, about 0.5 mg, about 0.6 mg, about 0.7 mg, about 0.8 mg, about 0.9 mg, about 1 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, or about 2.5 mg.

In one embodiment, for any of the methods disclosed in this application, KX-01 is administered to an affected area of the subject at a dose of about 0.5 mg, about 0.6 mg, about 0.7 mg, about 0.8 mg, about 0.9 mg, about 1 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, or about 2.5 mg.

In one embodiment, for any of the methods disclosed in this application, KX-01 is administered to an affected area of the subject at a dose from about 0.0003 mg/cm$^2$ to about 10 mg/cm$^2$.

In one embodiment, for any of the methods disclosed in this application, KX-01 is administered to an affected area of the subject at a dose from about 0.001 mg/cm$^2$ to about 0.4 mg/cm$^2$.

In one embodiment, for any of the methods disclosed in this application, KX-01 is administered to an affected area of the subject at a dose from about 0.005 mg/cm$^2$ to about 0.1 mg/cm$^2$.

In one embodiment, for any of the methods disclosed in this application, KX-01 is administered to an affected area of the subject at a dose from about 0.005 mg/cm$^2$ to about 0.02 mg/cm$^2$.

In one embodiment, for any of the methods disclosed in this application, KX-01 is administered to an affected area of the subject at a dose from about 0.025 mg/cm$^2$ to about 0.1 mg/cm$^2$.

In one embodiment, for any of the methods disclosed in this application, KX-01 is administered to an affected area of the subject at a dose of about 0.001 mg/cm$^2$, about 0.002 mg/cm$^2$, about 0.003 mg/cm$^2$, about 0.004 mg/cm$^2$, about 0.005 mg/cm$^2$, about 0.006 mg/cm$^2$, about 0.007 mg/cm$^2$, about 0.008 mg/cm$^2$, about 0.009 mg/cm$^2$, about 0.01 mg/cm$^2$, about 0.02 mg/cm$^2$, about 0.03 mg/cm$^2$, about 0.04 mg/cm$^2$, about 0.05 mg/cm$^2$, about 0.06 mg/cm$^2$, about 0.07 mg/cm$^2$, about 0.08 mg/cm$^2$, about 0.09 mg/cm$^2$, about 0.1 mg/cm$^2$, about 0.15 mg/cm$^2$, about 0.2 mg/cm$^2$, about 0.25 mg/cm$^2$, about 0.3 mg/cm$^2$, about 0.35 mg/cm$^2$, or about 0.4 mg/cm$^2$.

In one embodiment, for any of the methods disclosed in this application, KX-01 is administered to an affected area of the subject at a dose of about 0.005 mg/cm$^2$, about 0.006 mg/cm$^2$, about 0.007 mg/cm$^2$, about 0.008 mg/cm$^2$, about 0.009 mg/cm$^2$, about 0.01 mg/cm$^2$, about 0.015 mg/cm$^2$, about 0.02 mg/cm$^2$, about 0.025 mg/cm$^2$, about 0.03 mg/cm$^2$, about 0.035 mg/cm$^2$, about 0.04 mg/cm$^2$, about 0.045 mg/cm$^2$, about 0.05 mg/cm$^2$, about 0.055 mg/cm$^2$, about 0.06 mg/cm$^2$, about 0.065 mg/cm$^2$, about 0.07 mg/cm$^2$, about 0.075 mg/cm$^2$, about 0.08 mg/cm$^2$, about 0.085 mg/cm$^2$, about 0.09 mg/cm$^2$, about 0.095 mg/cm$^2$, or about 0.1 mg/cm$^2$.

In one embodiment, for any of the methods disclosed in this application, KX-01 is administered to an affected area of the subject at a dose of about 0.025 mg/cm$^2$, about 0.02 mg/cm$^2$, about 0.015 mg/cm$^2$, about 0.01 mg/cm$^2$, about 0.005 mg/cm$^2$, about 0.002 mg/cm$^2$, about 0.001 mg/cm$^2$, about 0.0005 mg/cm$^2$, about 0.0002 mg/cm$^2$, or about 0.0001 mg/cm$^2$.

In one embodiment, for any of the methods disclosed in this application, KX-01 is administered to an affected area of the subject at a dose of about 0.025 mg/cm$^2$.

In one embodiment, for any of the methods disclosed in this application, KX-01 is administered to an affected area of the subject at a dose of about 0.02 mg/cm$^2$.

In one embodiment, for any of the methods disclosed in this application, KX-01 is administered to an affected area of the subject at a dose of about 0.015 mg/cm$^2$.

In one embodiment, for any of the methods disclosed in this application, KX-01 is administered to an affected area of the subject at a dose of about 0.01 mg/cm$^2$.

In one embodiment, for any of the methods disclosed in this application, KX-01 is administered to an affected area of the subject at a dose of about 0.005 mg/cm$^2$.

In one embodiment, for any of the methods disclosed in this application, KX-01 is administered to an affected area of the subject at a dose of about 0.002 mg/cm$^2$.

In one embodiment, for any of the methods disclosed in this application, KX-01 is administered to an affected area of the subject at a dose of about 0.001 mg/cm$^2$.

In one embodiment, for any of the methods disclosed in this application, KX-01 is administered to an affected area of the subject at a dose of about 0.0005 mg/cm$^2$.

In one embodiment, for any of the methods disclosed in this application, KX-01 is administered to an affected area of the subject at a dose of about 0.0002 mg/cm$^2$.

In one embodiment, for any of the methods disclosed in this application, KX-01 is administered to an affected area of the subject at a dose of about 0.0001 mg/cm$^2$.

In one embodiment, for any of the methods disclosed in this application, KX-01 is administered to an affected area of the subject that is about 0.01 cm$^2$ to about 300 cm$^2$.

In one embodiment, for any of the methods disclosed in this application, KX-01 is administered to an affected area of the subject that is about 0.01 cm$^2$ to about 200 cm$^2$, about 0.01 cm$^2$ to about 100 cm$^2$, about 0.01 cm$^2$ to about 75 cm$^2$, about 0.01 cm$^2$ to about 50 cm$^2$, or about 0.01 cm$^2$ to about 25 cm$^2$.

In one embodiment, for any of the methods disclosed in this application, KX-01 is administered to an affected area of the subject that is about 0.1 cm$^2$ to about 300 cm$^2$, is about 0.1 cm$^2$ to about 200 cm$^2$, about 0.1 cm$^2$ to about 100 cm$^2$, about 0.1 cm$^2$ to about 75 cm$^2$, about 0.1 cm$^2$ to about 50 cm$^2$, or about 0.1 cm$^2$ to about 25 cm$^2$.

In one embodiment, for any of the methods disclosed in this application, KX-01 is administered to an affected area of the subject that is about 1 cm$^2$ to about 300 cm$^2$, about 1 cm$^2$ to about 200 cm$^2$, about 1 cm$^2$ to about 100 cm$^2$, about 1 cm$^2$ to about 75 cm$^2$, about 1 cm$^2$ to about 50 cm$^2$, or about 1 cm$^2$ to about 25 cm$^2$.

In one embodiment, for any of the methods disclosed in this application, KX-01 is administered to an affected area of the subject that is about 10 cm$^2$ to about 300 cm$^2$, about 10 cm$^2$ to about 200 cm$^2$, about 10 cm$^2$ to about 100 cm$^2$, about 10 cm$^2$ to about 75 cm$^2$, about 10 cm$^2$ to about 50 cm$^2$, or about 10 cm$^2$ to about 25 cm$^2$.

In one embodiment, for any of the methods disclosed in this application, KX-01 is administered to an affected area of the subject that is about 25 cm$^2$ to about 300 cm$^2$, about 25 cm$^2$ to about 200 cm$^2$, about 25 cm$^2$ to about 100 cm$^2$, about 25 cm$^2$ to about 75 cm$^2$, or about 25 cm$^2$ to about 50 cm$^2$.

In one embodiment, for any of the methods disclosed in this application, KX-01 is administered to an affected area of the subject that is the affected area is about 25 cm$^2$ to about 100 cm$^2$, about 25 cm$^2$ to about 90 cm$^2$, about 25 cm$^2$ to about 80 cm$^2$, or about 25 cm$^2$ to about 70 cm$^2$, about 25 cm$^2$ to about 60 cm$^2$, about 25 cm$^2$ to about 50 cm$^2$, about 25 cm$^2$ to about 40 cm$^2$, or about 25 cm$^2$ to about 30 cm$^2$.

In one embodiment, for any of the methods disclosed in this application, KX-01 is administered to an affected area of the subject that is about 0.01 cm$^2$, 0.1 cm$^2$, 1 cm$^2$, 2 cm$^2$, 3 cm$^2$, 4 cm$^2$, 5 cm$^2$, 6 cm$^2$, 7 cm$^2$, 8 cm$^2$, 9 cm$^2$, 10 cm$^2$, 15 cm², 20 cm², 25 cm², 30 cm², 35 cm², 40 cm², 45 cm², 50 cm², 55 cm², 60 cm², 65 cm², 70 cm², 75 cm², 80 cm², 85 cm², 90 cm², 95 cm², or 100 cm².

In one embodiment, for any of the methods disclosed in this application, KX-01 is administered to an affected area of the subject that is about 25 cm², about 30 cm², about 35 cm², about 40 cm², about 45 cm², about 50 cm², about 55 cm², about 60 cm², about 65 cm², about 70 cm², about 75 cm², about 80 cm², about 85 cm², about 90 cm², about 95 cm², or about 100 cm².

In one embodiment, for any of the methods disclosed in this application, KX-01 is administered to an affected area of the subject, wherein the affected area is the skin.

In one embodiment, for any of the methods disclosed in this application, KX-01 is administered to an affected area of the subject, wherein the affected area of the skin is located at one or more locations independently selected from the scalp, forehead, forearm, face, nose, ears, eye lids, lips, neck, arms, hands, trunk, legs, and feet.

In one embodiment, for any of the methods disclosed in this application, the subject has more than one affected area.

In one embodiment, for any of the methods disclosed in this application, the subject has more than one affected area located at one or more locations independently selected from the scalp, forehead, forearm, face, nose, ears, eye lids, lips, neck, arms, hands, trunk, legs, and feet.

In one embodiment, for any of the methods disclosed in this application, KX-01 is administered once a week, once every three days, once every two days, once a day, twice a day, three times a day, or four times a day.

In one embodiment, for any of the methods disclosed in this application, KX-01 is administered once a day or twice a day.

In one embodiment, for any of the methods disclosed in this application, KX-01 is administered once a day.

In one embodiment, for any of the methods disclosed in this application, KX-01 is administered for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 days.

In one embodiment, for any of the methods disclosed in this application, KX-01 is administered for 1, 2, 3, 4, 5, 6, 7, 8, 9, 10, 11, 12, 13, 14, 15, 16, 17, 18, 19, 20 or 21 days.

In one embodiment, for any of the methods disclosed in this application, KX-01 is administered for 1, 2, 3, 4, 5, 6, 7, 8, 9, 10, 11, 12, 13, or 14 days.

In one embodiment, for any of the methods disclosed in this application, KX-01 is administered for 1, 2, 3, 4, 5, 6, or 7 days.

In one embodiment, for any of the methods disclosed in this application, KX-01 is administered for 1, 2, 3, 4 or 5 days.

In one embodiment, for any of the methods disclosed in this application, KX-01 is administered for 1 day.

In one embodiment, for any of the methods disclosed in this application, KX-01 is administered for 2 days.

In one embodiment, for any of the methods disclosed in this application, KX-01 is administered for 3 days.

In one embodiment, for any of the methods disclosed in this application, KX-01 is administered for 4 days.

In one embodiment, for any of the methods disclosed in this application, KX-01 is administered for 5 days.

In one embodiment, for any of the methods disclosed in this application, KX-01 is administered for 1, 2, 3, 4, 5, or 6 days per week.

In one embodiment, for any of the methods disclosed in this application, KX-01 is administered for 2, 3, 4, 5, or 6 days per week.

In one embodiment, for any of the methods disclosed in this application, KX-01 is administered once or twice daily continuously for more than one day per week, followed by discontinuation of the administration for the rest of the week.

In one embodiment, for any of the methods disclosed in this application, KX-01 is administered once or twice daily every other day.

In one embodiment, for any of the methods disclosed in this application, KX-01 is administered once or twice daily every three days, every four days, every five days, every six days, or every seven days.

In one embodiment, for any of the methods disclosed in this application, KX-01 is administered once or twice daily for two days in a row every three days, every four days, every five days, every six days, or every seven days.

In one embodiment, for any of the methods disclosed in this application, KX-01 is administered once or twice daily for three days in a row every four days, every five days, every six days, or every seven days.

In one embodiment, for any of the methods disclosed in this application, KX-01 is administered once or twice daily for four days in a row every five days, every six days, or every seven days.

In one embodiment, for any of the methods disclosed in this application, KX-01 is administered until the actinic keratosis is fully treated.

In one embodiment, for any of the methods disclosed in this application, KX-01 is administered until the actinic keratosis is fully treated, i.e., the actinic keratosis is clear from the affected area of the subject.

In one embodiment, for any of the methods disclosed in this application, KX-01 is administered topically.

In one embodiment, for any of the methods disclosed in this application, the administration of KX-01 reduces the number and/or severity of local skin reactions or other adverse side effects in the subject compared to other treatments of actinic keratosis. In one embodiment, the other treatment of actinic keratosis comprises the topical administration of ingenol mebutate.

In one embodiment, for any of the methods disclosed in this application, the administration of KX-01 reduces the number of the subjects that have local skin reactions or other adverse side effects compared to other treatments of actinic keratosis.

In one embodiment, for any of the methods disclosed in this application, the local skin reaction is selected from the group selected from vesiculation, postulation, erosion, ulceration, redness, swelling, flaking, scaling, hard lumps, dryness, pus, and blistering.

In one embodiment, for any of the methods disclosed in this application, the other side effect is selected from the group consisting of application site pain, application site pruritus, application site irritation, application site swelling, application site burning sensation, application site infection, periorbital edema, nasopharyngitis, chills, sore throat, drooping eyes, puffy eyes, hypopigmentation, hyperpigmentation, and headache.

In one aspect, this application pertains at least in part, to KX-01 for use (e.g., topical use) in the treatment and/or prevention of actinic keratosis. In certain aspects, KX-01 is for use at the doses, dosing schedules, and/or one or more affected area in a subject in need thereof as described herein.

In one aspect, this application pertains at least in part, to use (e.g., topical use) of KX-01 in the treatment and/or prevention of actinic keratosis. In certain aspects, KX-01 is used at the doses, dosing schedules, and/or one or more affected area in a subject in need thereof as described herein.

In one aspect, this application pertains at least in part, to use of KX-01 in the manufacture of a medicament for the treatment and/or prevention of actinic keratosis. In certain aspects, KX-01 is used at the doses, dosing schedules, and/or one or more affected area in a subject in need thereof as described herein.

Unless explicitly indicated otherwise, the terms "KX-01" and "KX2-391" refer to the basic form of the compound, i.e., the "free base," which has the following structure:

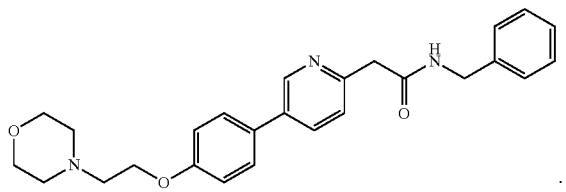 [SMILES: O=C(Cc1ccc(-c2ccc(OCCN3CCOCC3)cc2)cn1)NCc1ccccc1]

The term "KX-01 MSA" refers to the mesylate salt of KX-01, i.e., the salt compound resulting from reacting KX-01 with methane sulfonic acid.

"KX-01", as used herein, may also be called "KX01", "KX2-391", or "KX-2-391".

KX-01, and salts thereof, e.g., KX-01 MSA, and their preparation are disclosed in PCT Application Publication Nos. WO 2008/082637, WO 2008/144045, and WO 2010/135429. These publications are incorporated by reference herein in their entireties.

Actinic keratosis, i.e., "AK," is a common precancerous skin condition caused by excessive exposure to ultraviolet light. AKs are rough, dry, tan-, pink-, or red-colored blemishes (lesions) that often appear on the parts of the head, including the face, throat, neck, nose, forehead, ears, or lips. AKs may also appear or other body parts that receive prolonged, intense sunlight, e.g., the hands, the back, and other areas on the trunk and legs.

As used herein, the term "trunk" refers to the portion of a subject that is not an arm, a leg, or the head.

AKs are most common in fair-skinned, middle-aged or elderly individuals. A subject suffering from AKs may have a single lesion or multiple lesions. AK can lead to squamous cell carcinoma.

Clinical variants of AK include: classic (or common), hypertrophic (or hyperkeratotic), atrophic, AK with cutaneous horn, pigmented AK, actinic cheilitis, and Bowenoid AK. Unless explicitly indicated otherwise, the methods described herein are applicable to all clinical variants, including those listed herein.

Treatments for AK include cryosurgery, surgical excision and/or scraping of the affected areas, photodynamic therapy, and topical formulations (e.g., creams, gels, patches, etc.) comprising a steroid, fluorouracil, diclofenac, imiquimod, 5-aminolaevulinic acid (Ameluz®).

The approved treatment for AK is Picato (Ingenol Mebutate)®, a gel containing ingenol mebutate (0.015% or 0.05%). The gel is applied to the affected areas on the face or scalp once daily for three consecutive days (0.015%), or on the trunk or extremities once daily for two consecutive days (0.05%).

The skin toxicity associated with the use of other AK treatments, such as with Picato (Ingenol Mebutate)®, is known to produce unwanted side effect or adverse reactions, i.e., local skin reactions (LSRs), which include vesiculation, postulation, erosion, ulceration, redness, swelling, flaking, scaling, hard lumps, dryness, pus, and blistering. Other side effects include application site pain, application site pruritus, application site irritation, application site swelling, application site burning sensation, application site infection, periorbital edema, nasopharyngitis, chills, sore throat, drooping eyes, puffy eyes, hypopigmentation, hyperpigmentation, and headache.

The phrase "until the actinic keratosis clears," as used herein, refers to the instance where the lesions on a subject suffering from AK have substantially or completely disappeared from the treated area on the subject. In one embodiment, "substantially," in this context, refers more than 50% of the AK lesions have disappeared from the treated area on the subject. In another embodiment, "substantially" refers more than 60% of the AK lesions have disappeared from the treated area on the subject. In another embodiment, "substantially" refers more than 70% of the AK lesions have disappeared from the treated area on the subject. In another embodiment, "substantially" refers more than 80% of the AK lesions have disappeared from the treated area on the subject. In another embodiment, "substantially" refers more than 90% of the AK lesions have disappeared from the treated area on the subject. In another embodiment, "substantially" refers more than 95% of the AK lesions have disappeared from the treated area on the subject. In another embodiment, "substantially" refers more than 99% of the AK lesions have disappeared from the treated area on the subject.

As used throughout the disclosure, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "comprising" is intended to mean that the method includes the recited elements, but do not exclude others. "Consisting essentially of" when used to define methods, shall mean excluding other elements of any essential significance to the combination when used for the intended purpose. Thus, a method consisting essentially of the elements as defined herein would not exclude substantial method steps. "Consisting of" shall mean excluding more than substantial method steps. Embodiments defined by each of these transition terms are within the scope of this application.

Unless explicitly indicated otherwise, the terms "approximately" and "about" are synonymous. In one embodiment, "approximately" and "about" refer to the recited amount, value, or duration ±5%, ±4.5%, ±4%, ±3.5%, ±3%, ±2.5%, ±2%, ±1.75%, ±1.5%, ±1.25%, ±1%, ±0.9%, ±0.8%, ±0.7%, ±0.6%, ±0.5%±0.4%, ±0.3%, ±0.2%, ±0.1%, ±0.09%, ±0.08%, ±0.07%, ±0.06%, ±0.05%, ±0.04%, ±0.03%, ±0.02%, or ±0.01%. In another embodiment, "approximately" and "about" refer to the listed amount, value, or duration ±2.5%, ±2%, ±1.75%, ±1.5%, ±1.25%, ±1%, ±0.9%, ±0.8%, ±0.7%, ±0.6%, ±0.5%. In yet another embodiment, "approximately" and "about" refer to the listed amount, value, or duration ±1%. In yet another embodiment, "approximately" and "about" refer to the listed amount, value, or duration ±0.5%. In yet another embodiment, "approximately" and "about" refer to the listed amount, value, or duration ±0.1%.

The term "subject" includes any living organism that has actinic keratosis, or is at a risk of developing actinic keratosis. In one embodiment, the term "subject" refers to a mammal that has actinic keratosis, or is at a risk of developing actinic keratosis. In one embodiment, the term subject refers to a human being that has actinic keratosis, or is at a risk of developing actinic keratosis. The term "patient" is meant to be synonymous with "subject," unless explicitly indicated otherwise.

The term "therapeutically effective amount", as used herein, refers to an amount of a pharmaceutical agent, e.g., KX-01, to treat, ameliorate, or prevent an identified disease or condition, e.g., AK, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

For any compound, the therapeutically effective amount can be estimated in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. The dosage may vary within this range depending upon the dosage form employed and sensitivity of the subject.

Dosage and administration are adjusted to provide sufficient levels of the active ingredient or to maintain the desired effect. Factors which may be taken into account include the severity of the disease state, location of the disease on the subject, general health of the subject, age, weight, and gender of the subject, diet, time and frequency of administration, drug combination(s), reaction sensitivities, and tolerance/response to therapy. KX-01 may be administered every day, every other day, every three days, every four days, every five days, every six days, every week, biweekly, or once every two weeks depending on half-life and clearance rate.

For any of the methods described herein, KX-01 may be administered topically, intradermally, interepidermally, intragingivally, intraocularly, nasally, ophthalmically, percutaneously, periodontally, subconjuctivally, sublingually, transmucosally, or otically. In one embodiment, KX-01 may be administered topically.

All percentages and ratios used herein, unless otherwise indicated, are by weight.

Every document cited herein, including any cross referenced or related patent or application, is hereby incorporated herein by reference in its entirety unless expressly excluded or otherwise limited. The citation of any document is not an admission that it is prior art with respect to any subject matter disclosed or claimed herein or that it alone, or in any combination with any other reference or references, teaches, suggests or discloses any such subject matter. Further, to the extent that any meaning or definition of a term in this document conflicts with any meaning or definition of the same term in a document incorporated by reference, the meaning or definition assigned to that term in this document shall govern.

While particular embodiments of the disclosure have been illustrated and described, various other changes and modifications can be made without departing from the spirit and scope of the disclosure. The scope of the appended claims includes all such changes and modifications that are within the scope of this disclosure.

Other features and advantages of the present application are apparent from the different examples. The provided examples illustrate different components and methodology useful in practicing the present application.

The examples do not limit the claimed application. Based on the present disclosure the skilled artisan can identify and employ other components and methodology useful for practicing the present applications.

EXAMPLES

Two clinical studies (detailed in Examples 1 and 2) were conducted to evaluate the activity and safety of KX-01 administered topically in subjects with actinic keratosis. Preliminary data from these studies suggested that KX-01 demonstrates clinically relevant activity in the treatment of actinic keratosis of the face and scalp, and of the forearm. KX-01, when administered for 5 days, has a very good safety profile with limited systemic exposure. Local tolerability appears to be very good with local skin reactions (LSRs) that consist primarily of mild to moderate erythema and scaling. KX-01 was found to be safe.

Example 1—A Phase 1 Study of KX-01 Administered Topically for 3 or 5 Days to the Forearm A Phase 1, single-center, safety, tolerability and pharmacokinetic study of KX-01 was performed on subjects with AK on the dorsal forearm. This was an open-label, uncontrolled, nonrandomized, sequential group clinical trial conducted at a single investigational center in the United States. The primary objectives of the study were to assess the safety, tolerability and pharmacokinetics of KX-01 in subjects with AK. The secondary objective was to evaluate the activity of KX-01 administered topically to the dorsal forearm in subjects with AK.

Adult subjects of 18 years of age and older with clinically typical AK lesions in the dorsal forearm who met all inclusion criteria and did not meet an exclusion criterion were enrolled into sequential cohorts.

Cohort 1, N=4, 0.5 mg KX-01 topically administered to a 25 cm² area with 4-8 clinically typical AK lesions on the dorsal forearm, daily for 3 consecutive days.

Cohort 2, N=10, 2.0 mg KX-01 topically administered to a 100 cm² area with 8-16 clinically typical AK lesions on the dorsal forearm, daily for 3 consecutive days.

Cohort 3, N=8, 0.5 mg KX-01 topically administered to a 25 cm² area with 4-8 clinically typical AK lesions area of the dorsal forearm, daily for 5 consecutive days.

Cohort 4, N=8, 2.0 mg KX-01 topically administered to a 100 cm² area with 8-16 clinically typical AK lesions of the dorsal forearm, daily for 5 consecutive days.

KX-01 was administered topically on treatment days. All subjects were monitored for safety and tolerability that included LSRs, AEs, vital signs, clinical laboratory tests, ECGs, and physical examinations at baseline and at pre-defined time points during treatment and follow-up on days 1, 2, 3, 4, 5, 8, 10, 17, 31 and 45. AK lesion counts were recorded at baseline on days 4, 10, 17, 31, and 45. Standardized photography of the treatment area was performed. Plasma samples for pharmacokinetics were collected at preplanned time points on Days 1-8.

LSRs (erythema, flaking/scaling, crusting, swelling, vesiculation/pustulation, erosion/ulceration) were assessed by the investigator or trained designee using a 4-point scale according to the protocol. The subject's assessment of the symptoms (stinging/burning, pruritus) associated with irritation of the treatment area was evaluated on a 4-point scale (0=none, 1=mild, 2=moderate, 3=severe). Subjects were queried for spontaneously reported AEs at each study visit before assessment of LSRs. LSRs and AEs were reported separately. All LSRs were to be followed to resolution or stabilization.

A total of 30 subjects were enrolled and 29 subjects completed the study. The subject population consisted of 19 male and 11 female subjects. Overall mean age was 63.1 years and mean weight was 194.9 pounds. All except one subject were white. All were of non-Hispanic or Latino ethnicity. Demographics and baseline characteristics by cohort are summarized in Table 1.

TABLE 1

Demographics and Baseline Characteristics of Subjects

| Demographics and Baseline Characteristics | Cohort 1 (N = 4) 0.5 mg KX-01/ 25 cm² QD × 3 days | Cohort 2 (N = 10) 2 mg KX-01/ 100 cm² QD × 3 days | Cohort 3 (N = 8) 0.5 mg KX-01/ 25 cm² QD × 5 days | Cohort 4 (N = 8) 2 mg KX-01/ 100 cm² QD × 5 days |
|---|---|---|---|---|
| Mean Age (years) | 63.0 | 61.8 | 63.0 | 64.9 |
| Gender (M/F) | 3/1 | 6/4 | 5/3 | 5/3 |
| Race | | | | |
| White | 4 | 9 | 8 | 8 |
| Other | 0 | 1 | 0 | 0 |
| Mean Weight (lbs) | 200.8 | 180.2 | 215.0 | 190.3 |
| Number of Baseline AK Lesions - Median (Range) | 5.0 (4-5) | 11.5 (8-16) | 6.0 (5-6) | 11.0 (10-16) |

M = male;
F = female

Local tolerability was acceptable. All 30 subjects had LSRs as assessed by the Investigator. In general, LSRs appeared on day 2, tended to peak around day 5 for the 3-day treatment cohorts (Cohorts 1 and 2) and around day 10 for the 5-day treatment cohorts (Cohorts 3 and 4), before returning to or close to baseline. No subject had an LSR score of 4 in any category. No subject had a vesicle or pustule. Fifteen subjects had erythema and/or flaking/scaling with a score 1 or 2 at day 45 that were followed until resolution or stabilization. Maximum LSRs are displayed by category and cohort in Table 2.

Subjects were specifically inquired about stinging, burning and pruritus at the application site at every visit. The maximum scores for each symptom are summarized in Table 2. In general, symptoms arose as early as day 2, peaked in severity and incidence at day 8-day 10, and resolved by day 45. Two subjects (one in Cohort 2 and one in Cohort 4) who had mild to moderate symptoms are being followed to resolution or stabilization. There was one subject in Cohort 3 who had severe pruritus on Day 17 that reduced to mild severity at the next visit on Day 31 without requiring concomitant medication.

TABLE 2

Number of Subjects (%) with Maximum LSR Score by LSR Category and by Cohort

| | Cohort 1 (N = 4) 0.5 mg KX-01 25 cm² QD × 3 days | | | | | Cohort 2 (N = 10) 2 mg KX-01 100 cm² QD × 3 days | | | | | Cohort 3 (N = 8) 0.5 mg KX-01 25 cm² QD × 5 days | | | | | Cohort 4 (N = 8) 2 mg KX-01 100 cm² QD × 5 days | | | | |
|---|---|---|---|---|---|---|---|---|---|---|---|---|---|---|---|---|---|---|---|---|
| Max score | 0 | 1 | 2 | 3 | 4 | 0 | 1 | 2 | 3 | 4 | 0 | 1 | 2 | 3 | 4 | 0 | 1 | 2 | 3 | 4 |
| Max LSR Score as Assessed by Investigator | | | | | | | | | | | | | | | | | | | | |
| Erythema | 0 | 2 (50%) | 1 (25%) | 1 (25%) | 0 | 0 | 6 (60%) | 2 (20%) | 2 (20%) | 0 | 0 | 2 (25%) | 4 (50%) | 2 (25%) | 0 | 0 | 2 (25%) | 4 (50%) | 2 (25%) | 0 |
| Flaking/scaling | 0 | 3 (75%) | 0 | 1 (25%) | 0 | 1 (10%) | 2 (20%) | 1 (10%) | 6 (60%) | 0 | 0 | 2 (25%) | 2 (25%) | 4 (50%) | 0 | 0 | 2 (25%) | 4 (50%) | 2 (25%) | 0 |
| Crusting | 4 (100%) | 0 | 0 | 0 | 0 | 0 | 5 (50%) | 5 (50%) | 0 | 0 | 0 | 1 (13%) | 7 (88%) | 0 | 0 | 0 | 4 (50%) | 4 (50%) | 0 | 0 |
| Swelling | 4 (100%) | 0 | 0 | 0 | 0 | 8 (80%) | 2 (20%) | 0 | 0 | 0 | 4 (50%) | 1 (13%) | 0 | 3 (38%) | 0 | 1 (13%) | 6 (75%) | 1 (13%) | 0 | 0 |
| Vesicles/pustules | 4 (100%) | 0 | 0 | 0 | 0 | 10 (100%) | 0 | 0 | 0 | 0 | 8 (100%) | 0 | 0 | 0 | 0 | 8 (100%) | 0 | 0 | 0 | 0 |
| Erosions/ulcers | 4 (100%) | 0 | 0 | 0 | 0 | 10 (100%) | 0 | 0 | 0 | 0 | 8 (100%) | 0 | 0 | 0 | 0 | 7 (88%) | 1 (13%) | 0 | 0 | 0 |

TABLE 2-continued

Number of Subjects (%) with Maximum LSR Score by LSR Category and by Cohort

| | LSRs | | | | | | | | | | | | | | | | | | | |
|---|---|---|---|---|---|---|---|---|---|---|---|---|---|---|---|---|---|---|---|---|
| | Cohort 1 (N = 4) 0.5 mg KX-01 25 cm² QD × 3 days | | | | | Cohort 2 (N = 10) 2 mg KX-01 100 cm² QD × 3 days | | | | | Cohort 3 (N = 8) 0.5 mg KX-01 25 cm² QD × 5 days | | | | | Cohort 4 (N = 8) 2 mg KX-01 100 cm² QD × 5 days | | | | |
| | | | | | | | | | | Max score | | | | | | | | | | |
| | 0 | 1 | 2 | 3 | 4 | 0 | 1 | 2 | 3 | 4 | 0 | 1 | 2 | 3 | 4 | 0 | 1 | 2 | 3 | 4 |
| | Max LSR Score as Assessed by Subjects | | | | | | | | | | | | | | | | | | | |
| Stinging | 3 (75%) | 1 (25%) | 0 | 0 | | 8 (80%) | 2 (20%) | 0 | 0 | | 6 (75%) | 1 (13%) | 1 (13%) | 0 | | 5 (63%) | 3 (38%) | 0 | 0 | |
| Burning | 4 (100%) | 0 | 0 | 0 | | 6 (60%) | 3 (30%) | 1 (10%) | 0 | | 4 (50%) | 3 (38%) | 1 (13%) | 0 | | 4 (50%) | 4 (50%) | 0 | 0 | |
| Pruritus | 3 (75%) | 1 (25%) | 0 | 0 | | 4 (40%) | 6 (60%) | 0 | 0 | | 2 (25%) | 4 (50%) | 1 (13%) | 1 (13%) | | 0 | 4 (50%) | 4 (50%) | 0 | |

LSR = local skin reaction;
Max = maximum.
Investigator's Assessment of LSR, 5-point scale LSR score: 0 = none, 1 = minimal, 2 = mild, 3 = moderate, 4 = severe.
Subject's Assessment of LSR, 4-point scale LSR score: 0 = none, 1 = mild, 2 = moderate, 3 = severe.

As a post-hoc analysis of LSRs, a composite score was calculated by adding the scores of the 6 LSR categories for each subject as determined by the investigator at each assessment visit. The range of the possible composite scores is 0-24. FIG. 1 displays the mean composite scores over time by cohort.

Four of 30 subjects reported 10 treatment emergent adverse events (TEAEs). All TEAEs were mild to moderate, and responded to treatment when given. No TEAE was reported for Cohort 1. One subject in Cohort 2 had mild upper respiratory tract infection on days 38-44, that was not related to study drug. One subject in Cohort 3 had headache on day 2, back pain on Days 4-5, and urinary tract infection on days 6-14; these AEs were of mild severity and were considered possibly related to study drug. The same subject had mild arthralgia on days 16-49, moderate osteoarthritis on day 16-49, and moderate pain from injection of platelet-rich plasma for treatment of osteoarthritis on day 43-44 that was considered not related to study drug. In Cohort 4, one subject had basal cell carcinoma, not in the treatment area, of moderate severity on days 3-25 that was considered not related to study drug; this was removed surgically. Another subject reported moderate muscular weakness and myositis that were unrelated to study drug, but related to fenofibrate that was being taken for hyperlipidemia. Fenofibrate was discontinued. On follow-up, muscular weakness resolved and myositis improved but was still ongoing.

There was no serious adverse event (SAE) or death in the study. No one discontinued treatment or follow-up for adverse events. One subject in Cohort 2 withdrew consent for personal reasons after 1 day of study drug application.

Clinical Activity:

All 4 cohorts showed reductions in mean baseline AK lesion counts over time and some patients demonstrated complete clearance at day 45 (Table 3).

TABLE 3

Complete/Partial Clearance by Cohort and Summary of Median (Range) of AK Lesion Counts by Visit and Cohort, in KX01-AK-01-US

| Activity | Cohort 1 (N = 4) 0.5 mg KX-01/ 25 cm² QD × 3 days | Cohort 2 (N = 10) 2 mg KX-01/ 100 cm² QD × 3 days | Cohort 3 (N = 8) 0.5 mg KX-01/ 25 cm² QD × 5 days | Cohort 4 (N = 8) 2 mg KX-01/ 100 cm² QD × 5 days |
|---|---|---|---|---|
| Complete Clearance on Day 45[a] | 1/4 (25%) | 0/10 | 4/8 (50%) | 1/8 (13%) |
| Partial Clearance on Day 45[b] | 2/4 (50%) | 3/10 (30%) | 5/8 (63%) | 4/8 (50%) |
| Summary of Median (Min, Max) of AK Lesion Counts by Visit by Cohort | | | | |
| Day 1 (Baseline) | 5.0 (4, 5) | 11.5 (8, 16) | 6.0 (5, 6) | 11.0 (10, 16) |
| Day 4 | 5.0 (4, 5) | 9.0 (6, 16) | Not done | Not done |
| Day 10 | 5.0 (4, 5) | 7.0 (6, 11) | 5.0 (5, 6) | 10.0 (10, 10) |
| Day 17 | 4.5 (3, 5) | 7.0 (5, 15) | 5.0 (4, 6) | 10.0 (10, 11) |
| Day 31 | 3.5 (1, 5) | 7.0 (1, 15) | 1.0 (0, 6) | 6.0 (0, 11) |
| Day 45 | 2.5 (0, 4) | 4.0 (1, 10) | 0.5 (0, 4) | 4.5 (0, 12) |

[a]Complete Clearance - 100% reduction in AK lesions on Day 45 compared to Baseline.
[b]Partial Clearance - ≥75% reduction in AK lesions on Day 45 compared to Baseline.

This study provided preliminary evidence of clinical activity of topically administered KX-01 for AK treatment. The data also suggested that the 5-day regimen may provide better activity than the 3-day regimen as shown by higher rates of complete and partial clearance of AK for the subjects treated for 5 days. Local skin reactions appeared to be primarily mild in nature. The safety and activity findings from this study provided the impetus to proceed with a larger multicenter study.

Example 2a—A Phase 2a Study of KX-01 Administered Topically to the Face or Scalp An ongoing Phase 2a, open-label, multicenter, activity and safety study of KX-01 administered topically in subjects with AK on the face or scalp is described herein. The primary objective is to evaluate the activity of KX-01 administered topically to the face or scalp in subjects with AK by determining complete response rate, defined as 100% clearance on Day 57. Secondary objectives are to assess the activity of KX-01 administered topically during Days 1-57 based on reduction of AK lesion counts from baseline, assess the safety and tolerability and pharmacokinetics, and contrast the dose regimens (5-day treatment with 3-day treatment) in terms of activity and safety in subjects with AK on the face or scalp. This uncontrolled, nonrandomized trial is being conducted at 16 investigational sites in the United States. Enrollment is sequential for 2 cohorts of approximately 80 subjects each. Enrollment is closed for Cohort 1 and ongoing for Cohort 2. The two treatment cohorts are summarized below:

Cohort 1: 0.5 mg KX-01 administered topically to a contiguous treatment area of 25 $cm^2$ with 4-8 clinically typical AK lesions for 5 consecutive days Cohort 2: 0.5 mg KX-01 administered topically to a contiguous treatment area of 25 $cm^2$ with 4-8 clinically typical AK lesions for 3 consecutive days 0.5 mg KX-01 is administered topically to an area of 25 $cm^2$ on the face or scalp by site staff on treatment days. All subjects are monitored for safety and tolerability that included LSRs, hyperpigmentation, hypopigmentation, scarring, AEs, vital signs, clinical laboratory tests, ECGs, and physical examinations at baseline at predefined time points during treatment and follow-up on days 1, 2, 3, 4, 5, 8, 15, 29, and 57. AK lesion counts are recorded at baseline, days 8, 15, 29, and 57. Those who achieve complete clearance of AK on day 57 will be followed for AK lesion counts, LSRs and AEs at 3, 6, 9, and 12 months after day 57 during the recurrence follow-up period. Standardized photography of treatment area is performed at baseline, day 8 and day 57. Plasma samples are being collected at preplanned time points on days 1 and 5 for Cohort 1, and on days 1 and 3 for Cohort 2.

LSRs (erythema, flaking/scaling, crusting, swelling, vesiculation/pustulation, erosion/ulceration) are assessed by the Investigator or trained designee using a grading scale from 0 (not present) to 4 (worst) based on protocol-defined LSR grading criteria. Absence or presence of hyperpigmentation, hypopigmentation and scarring are also assessed. Application site reactions not classified as LSRs are reported as AEs. Subjects are queried for spontaneously reported AEs at each study visit before assessment of LSRs. LSRs and AEs are reported separately. All LSRs, pigmentation, and scarring in the treatment area will be followed to resolution or stabilization.

82 eligible subjects were enrolled in Cohort 1. Demographics and baseline characteristics of subjects are displayed in Table 4. There has been no discontinuation prior to day 57. As this study is ongoing, the data presented are to be considered preliminary. Data from Cohort 2 (3-day dosing) are not yet available.

TABLE 4

Demographics and Baseline Characteristics of Subjects in Cohort 1

| Demographics and Baseline Characteristics | Cohort 1 (N = 82) 0.5 mg KX-01, 25 $cm^2$ QD × 5 days |
|---|---|
| Mean Age (years) | 69.0 |
| Gender: Male/Female | 74/8 |
| Race - White | 82 |
| Ethnicity - Hispanic or Latino/Non - Hispanic or Latino | 2/80 |
| Skin Type I/II/III/IVN/VI | 11/37/26/7/1/0 |
| AK lesion count at Baseline - Median (Min, Max) | 6.0 (4, 8) |
| Mean Weight (pounds) | 194.07 |

Of the 67 subjects who had day 57 visits, 7 had no LSR in the treatment area throughout the study. The majority of subjects were found to have erythema ($60/67$, 90%) and flaking/scaling ($47/67$, 70%). Most of these LSRs were scored at 1 and 2. Crusting was observed in $26/67$ (39%) of subjects and was mostly scored at 1. Swelling was reported in $14/67$ (21%) subjects. All swellings were scored at 1 except for two subjects, one scored at 2, and another scored at 3. Three subjects had vesiculation/pustulation and 9 subjects had erosion/ulceration. LSRs were generally observable from day 3 and reached a maximum score by day 5 and day 8 before decreasing to or close to baseline by day 29 and 57. Of the 60 subjects who had LSRs, all but 8 subjects had LSRs return to baseline at day 57. These 8 subjects had erythema of score 1 or 2, flaking/scaling, and/or crusting of score 1, and were being followed until resolution or stabilization by the investigators.

A detailed summary of local skin reactions (LSRs) from this study KX01-AK-002 is provided below in Table 5.

TABLE 5

Summary of Local Skin Reactions by Visit Evaluable Set in Cohort 1

| Visit Grade | Erythema | Flaking/Scaling | Crusting | Swelling | Vesiculation/Pustulation | Erosion/Ulceration |
|---|---|---|---|---|---|---|
| Day 1, n (%) | | | | | | |
| 0 | 56/67 (84) | 55/67 (82) | 62/67 (93) | 67/67 (100) | 67/67 (100) | 67/67 (100) |
| 1 | 11/67 (16) | 12/67 (18) | 5/67 (7) | 0 | 0 | 0 |
| 2 | 0 | 0 | 0 | 0 | 0 | 0 |
| 3 | 0 | 0 | 0 | 0 | 0 | 0 |
| 4 | 0 | 0 | 0 | 0 | 0 | 0 |
| Day 2, n (%) | | | | | | |
| 0 | 44/67 (66) | 51/67 (76) | 64/67 (96) | 67/67 (100) | 67/67 (100) | 67/67 (100) |
| 1 | 20/67 (30) | 15/67 (22) | 2/67 (3) | 0 | 0 | 0 |
| 2 | 3/67 (4) | 1/67 (1) | 1/67 (1) | 0 | 0 | 0 |

TABLE 5-continued

Summary of Local Skin Reactions by Visit Evaluable Set in Cohort 1

| Visit Grade | Erythema | Flaking/ Scaling | Crusting | Swelling | Vesiculation/ Pustulation | Erosion/ Ulceration |
|---|---|---|---|---|---|---|
| 3 | 0 | 0 | 0 | 0 | 0 | 0 |
| 4 | 0 | 0 | 0 | 0 | 0 | 0 |
| Day 3, n (%) | | | | | | |
| 0 | 32/67 (48) | 46/67 (69) | 63/67 (94) | 67/67 (100) | 67/67 (100) | 66/67 (99) |
| 1 | 24/67 (36) | 14/67 (21) | 3/67 (4) | 0 | 0 | 1/67 (1) |
| 2 | 10/67 (15) | 5/67 (7) | 1/67 (1) | 0 | 0 | 0 |
| 3 | 1/67 (1) | 2/67 (3) | 0 | 0 | 0 | 0 |
| 4 | 0 | 0 | 0 | 0 | 0 | 0 |
| Day 4, n (%) | | | | | | |
| 0 | 19/67 (28) | 43/67 (64) | 61/67 (91) | 65/67 (97) | 66/67 (99) | 65/67 (97) |
| 1 | 26/67 (39) | 16/67 (24) | 4/67 (6) | 2/67 (3) | 1/67 (1) | 2/67 (3) |
| 2 | 17/67 (25) | 5/67 (7) | 2/67 (3) | 0 | 0 | 0 |
| 3 | 5/67 (7) | 3/67 (4) | 0 | 0 | 0 | 0 |
| 4 | 0 | 0 | 0 | 0 | 0 | 0 |
| Day 5, n (%) | | | | | | |
| 0 | 12/67 (18) | 35/67 (52) | 56/67 (84) | 58/67 (87) | 65/67 (97) | 61/67 (91) |
| 1 | 19/67 (28) | 21/67 (31) | 9/67 (13) | 7/67 (10) | 2/67 (3) | 6/67 (9) |
| 2 | 27/67 (40) | 9/67 (13) | 2/67 (3) | 1/67 (1) | 0 | 0 |
| 3 | 9/67 (13) | 2/67 (3) | 0 | 1/67 (1) | 0 | 0 |
| 4 | 0 | 0 | 0 | 0 | 0 | 0 |
| Day 8, n (%) | | | | | | |
| 0 | 14/67 (21) | 26/67 (39) | 51/67 (76) | 64/67 (96) | 67/67 (100) | 65/67 (97) |
| 1 | 24/67 (36) | 18/67 (27) | 15/67 (22) | 3/67 (4) | 0 | 1/67 (1) |
| 2 | 25/67 (37) | 15/67 (22) | 1/67 (1) | 0 | 0 | 1/67 (1) |
| 3 | 4/67 (6) | 8/67 (12) | 0 | 0 | 0 | 0 |
| 4 | 0 | 0 | 0 | 0 | 0 | 0 |
| Day 15, n (%) | | | | | | |
| 0 | 27/67 (40) | 39/67 (58) | 63/67 (94) | 67/67 (100) | 67/67 (100) | 66/67 (99) |
| 1 | 25/67 (37) | 14/67 (21) | 4/67 (6) | 0 | 0 | 1/67 (1) |
| 2 | 13/67 (19) | 9/67 (13) | 0 | 0 | 0 | 0 |
| 3 | 2/67 (3) | 5/67 (7) | 0 | 0 | 0 | 0 |
| 4 | 0 | 0 | 0 | 0 | 0 | 0 |
| Day 29, n (%) | | | | | | |
| 0 | 45/67 (67) | 51/67 (76) | 65/67 (97) | 66/67 (99) | 67/67 (100) | 67/67 (100) |
| 1 | 18/67 (27) | 13/67 (19) | 2/67 (3) | 1/67 (1) | 0 | 0 |
| 2 | 4/67 (6) | 2/67 (3) | 0 | 0 | 0 | 0 |
| 3 | 0 | 1/67 (1) | 0 | 0 | 0 | 0 |
| 4 | 0 | 0 | 0 | 0 | 0 | 0 |
| Day 57, n (%) | | | | | | |
| 0 | 53/67 (79) | 57/67 (85) | 63/67 (94) | 67/67 (100) | 67/67 (100) | 67/67 (100) |
| 1 | 12/67 (18) | 10/67 (15) | 4/67 (6) | 0 | 0 | 0 |
| 2 | 2/67 (3) | 0 | 0 | 0 | 0 | 0 |
| 3 | 0 | 0 | 0 | 0 | 0 | 0 |
| 4 | 0 | 0 | 0 | 0 | 0 | 0 |

Note

1: Cohort 1 = 25 cm^2 treatment area/5 consecutive treatment days/0.5 mg KX-01 administered topically.

2: Data are presented as number of subjects with a specific finding/number of subjects assessed at each visit.

Percentage calculated is indicated in parenthesis.

Table 6 presents the maximum post-dose LSR score and the maximal LSR scores experienced in the combined Picato (Ingenol Mebutate)® Phase 3 registration trials for the treatment of AK of the face and scalp. The data suggest that 5-day treatment with KX-01 administered topically may have a more benign local safety profile compared to that reported for Picato (Ingenol Mebutate).

TABLE 6

Side-by-Side Summary of Maximal Local Skin Reactions Post-Baseline for Picato (Ingenol Mebutate) ®

| Local Skin Responses | Grade | Pep005 Gel 0.015%[a] N = 274 | KX-01[b] N = 67 |
|---|---|---|---|
| Erythema | 0 | 1 (<1%) | 7 (10%) |
| | 1 | 25 (9%) | 16 (24%) |
| | 2 | 56 (20%) | 32 (48%) |
| | 3 | 125 (46%) | 12 (18%) |
| | 4 | 66 (24%) | 0 (0%) |
| Flaking/ Scaling | 0 | 7 (3%) | 20 (30%) |
| | 1 | 52 (19%) | 14 (21%) |
| | 2 | 91 (33%) | 20 (30%) |
| | 3 | 98 (36%) | 13 (19%) |
| | 4 | 25 (9%) | 0 (0%) |
| Crusting | 0 | 44 (16%) | 41 (61%) |
| | 1 | 85 (31%) | 20 (30%) |
| | 2 | 64 (23%) | 6 (9%) |
| | 3 | 64 (23%) | 0 (0%) |
| | 4 | 16 (6%) | 0 (0%) |
| Swelling | 0 | 56 (20%) | 53 (79%) |
| | 1 | 88 (32%) | 12 (18%) |
| | 2 | 67 (25%) | 1 (1%) |
| | 3 | 48 (18%) | 1 (1%) |
| | 4 | 14 (5%) | 0 (0%) |
| Vesiculation/ Pustulation | 0 | 119 (43%) | 64 (96%) |
| | 1 | 36 (13%) | 3 (4%) |
| | 2 | 53 (19%) | 0 (0%) |
| | 3 | 50 (18%) | 0 (0%) |
| | 4 | 15 (6%) | 0 (0%) |
| Erosion/ Ulceration | 0 | 186 (68%) | 57 (85%) |
| | 1 | 55 (20%) | 9 (13%) |
| | 2 | 26 (10%) | 1 (1%) |
| | 3 | 5 (2%) | 0 (0%) |
| | 4 | 1 (<1%) | 0 (0%) |

[a]Source: NDA 202833; Statistical Review and Evaluation Pep005 (Ingenol Mebutate) gel, 0.015%; Table 9.
[b]Values are number of subjects in the Evaluable Set, categorized per their maximal post-baseline LSR grade. Percentages are based on the number of subjects.

Figure 2:
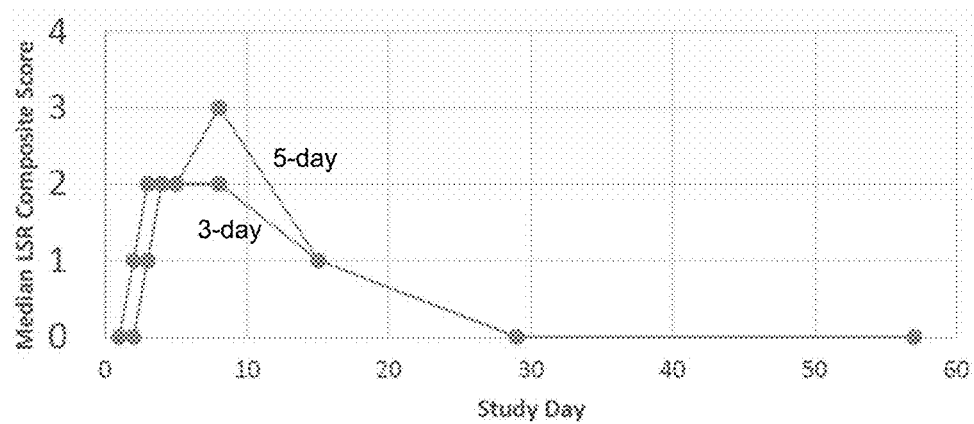
FIG. 2. Mean LSR composite scores vs. time—Phase 2a study of KX-01 administered topically. 0.5 mg KX-01 topically administered to a contiguous treatment area of 25 cm² with 4-8 typical AK lesions for 3 or 5 consecutive days.

As a post-hoc analysis of LSRs, a composite score was calculated by adding the scores of the 6 LSR categories for each subject at each assessment visit. The range of possible composite scores is 0-24. FIG. 2 displays the mean composite scores over time in Cohort 1.

All 82 subjects entered into Cohort 1 were included in the AE analysis. Twenty-six of 82 subjects in Cohort 1 reported a total of 54 TEAEs. All TEAEs were mild to moderate except for one severe case of small bowel obstruction that was reported as an SAE (discussed below). Seven subjects reported 12 TEAEs that were considered related to KX-01. There were 6 cases of application site reaction which included 1 mild tenderness, 2 mild stinging, and 3 mild pruritus. Other treatment-related AEs were 2 cases of mild dizziness, 1 mild darkening of hair color near the treatment area and 1 mild headache. There was a case of "worsening of elevated alanine transaminase" from a baseline of 58 IU/mL to 61 IU/mL on day 22. A case of mild conjunctivitis near the treatment area was reported on day 4 and lasted until day 5. The subject clarified that there was only mucus secretion from the eye due to use of contact lens. There was no associated redness, itch, pain or swelling, and KX-01 did not get into the eye.

There were 3 SAEs that occurred in 2 subjects, none of which were considered related to study drug. All SAEs required hospitalization. One subject was an 84-year old male subject who had small bowel obstruction on day 56, transurethral resection of prostate (TURP) for benign prostatic hypertrophy (BPH) on day 67, and postoperative cardiac ischemia on day 72. He recovered thereafter. Another subject was a 67-year old white male who was hospitalized for TURP for BPH on day 17. He recovered uneventfully.

There was one case of cancer that was unrelated to study drug—a 61-year old man who was diagnosed to have squamous cell carcinoma not in the treatment area on day 3 that was subsequently excised. This AE was not considered serious.

Among the enrolled subjects, 67 have reached the day 57 visit. Twenty-four of 67 subjects (36%, 95% CI (confidence interval): 24%-47%) achieved the primary endpoint defined as 100% clearance of AK lesions in the treatment area on day 57. Of the 35 subjects who received treatment on their faces, 15 (43%, 95% CI: 26%-59%) achieved 100% clearance, while 9 of 32 subjects (28%, 95% CI: 13%-44%) who received treatment on their scalp achieved 100% clearance.

Thirty-four of 67 subjects (51%, 95% CI: 39%-63%) had at least 75% reduction of AK lesions on day 57 compared to baseline; 21/35 (60%, 95% CI: 44%-76%) who had treatment on the face and 13/32 (41%, 95% CI: 24%-58%) who had treatment on the scalp. These data are summarized in Table 7.

TABLE 7

Analysis of Clearance Rate at Day 57—Evaluable Set in Cohort 1

| Clearance (a) | Treatment Area | Number of Subjects with Specified Clearance at Day 57 | Total Number of Subjects at Day 57 | Binomial Proportion | Wald 95% Lower Confidence Limit | Wald 95% Upper Confidence Limit |
|---|---|---|---|---|---|---|
| 100% | Face | 15 | 35 | 0.43 | 0.26 | 0.59 |
| | Scalp | 9 | 32 | 0.28 | 0.13 | 0.44 |
| | Overall | 24 | 67 | 0.36 | 0.24 | 0.47 |
| >=75% | Face | 21 | 35 | 0.60 | 0.44 | 0.76 |
| | Scalp | 13 | 32 | 0.41 | 0.24 | 0.58 |
| | Overall | 34 | 67 | 0.51 | 0.39 | 0.63 |

Note
1: Data cutoff date is 12 OCT. 2016.
2: Cohort 1/cm^2 treatment area/5 consecutive treatment thy s/0.5 mg KX-01 administered topically.
(a) Clearance is calculated relative to assessment at Day 1 visit.

Activity of KX-01 in terms of reduction of AK lesion counts is summarized in Table 8. Over the 57-day observation period, there was a progressive decline in median lesion count, from 6.0 to 2.0.

TABLE 8

Summary of AK Lesion Counts by Visit in Cohort 1, KX01-AK-002

| AK Lesion Counts | Day 1 | Day 8 | Day 15 | Day 29 | Day 57 |
|---|---|---|---|---|---|
| N | 67 | 60[a] | 63[a] | 67 | 67 |
| Median | 6.0 | 5.0 | 4.0 | 2.0 | 2.0 |
| Min, Max | 4, 8 | 0, 10 | 0, 9 | 0, 8 | 0, 9 |

KX-01 administered topically once daily for 5 days appears to be safe and well tolerated. There were few treatment-related adverse events and no treatment-related severe or serious adverse events.

The 5-day dosing regimen of KX-01 was associated with mild and reversible LSRs consisting primarily of erythema and flaking/scaling. In this study, no Grade 4 LSRs were observed after 5 days of treatment with KX-01.

Preliminary results (Example 1, Example 2a, and Example 2b) indicate that KX-01 administered topically once daily for up to 5 days demonstrates clinically relevant activity in the treatment of AK of the dorsal forearm, as well as both the face and scalp. The data suggest that the 5-day regimen of KX-01 has greater activity than the 3-day regimen.

Cross-study tabulation of results with those published for Picato (Ingenol Mebutate) suggests that the activity of the 5-day treatment regimen of KX-01 administered topically may be comparable to that observed in the Picato (Ingenol Mebutate) Phase 3 studies (Table 9).

TABLE 9

Cross-Study Tabulation of Complete Clearance Rates-KX-01 and Picato (Ingenol Mebutate) ®

| Anatomical Location | KX-01 3-day Topical Regimen[a] | KX-01 5-day Topical Regimen[a] | Picato Gel[b] | Picato Gel[b] |
|---|---|---|---|---|
| Arm (25 cm² area) | 1/4 (25%) | 4/8 (50%) | Study 3 22/84 (26%) | Study 4 27/59 (46%) |
| Face | TBD | 15/35 (43%) | Study 1 46/109 (42%) | Study 2 58/111 (52%) |
| Scalp | TBD | 9/32 (28%) | Study 1 4/26 (15%) | Study 2 9/31 (29%) |

[a]Studies KX01-AK-01-US and KX01-AK-002, data cut-off date is 12 Oct. 2016.
[b]Picato (Ingenol Mebutate) ® Prescribing Information, September 2016.

Pharmacokinetic results following up to 5 consecutive days of treatment with KX-01 showed low systemic exposure (<1 ng/mL) and limited drug accumulation in the majority of subjects. The data suggest that 5 days of topical treatment with KX-01 has optimal activity and safety.

Figure 5:
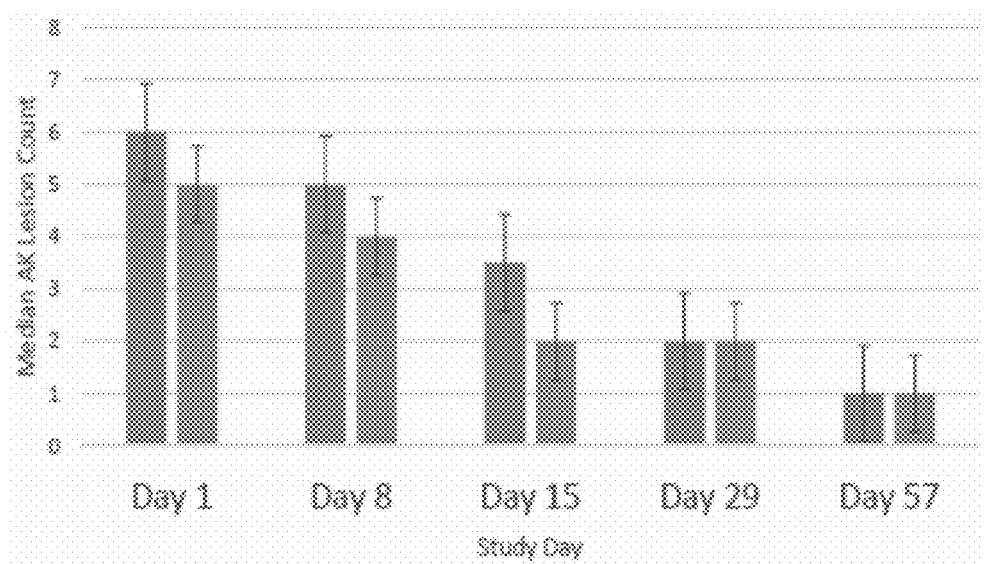
FIG. 5. A bar graph displaying median AK lesion counts over time (the left bar of each pair of bars shows results from the 5-day treatment and the right bar from the 3-day treatment).

Example 2b—A Phase 2a Study of KX-01 Administered Topically to the Face or Scalp The Phase 2a trial described in Example 2a was completed with 84 eligible subjects enrolled in each of two cohorts: one cohort was subjected to the treatment for 5 consecutive days, and the other cohort was subjected to the treatment for 3 consecutive days. The results are described below and in FIG. 5.

TABLE 10

AK Clearance in the Two Cohort at Day 57 After Treatment

| Cohort | Clearance of AK at day 57 | Responders/Total Number (%) Face | Scalp | Overall |
|---|---|---|---|---|
| 5-day | 100% | 23/44 (52%) | 13/40 (33%) | 36/84 (43%) |
|  | ≥75% | 29/44 (66%) | 18/40 (45%) | 47/84 (56%) |
| 3-day | 100% | 20/66 (30%) | 7/18 (39%) | 27/84 (32%) |
|  | ≥75% | 35/66 (53%) | 9/18 (50%) | 44/84 (52%) |

TABLE 11

Side-by-Side Summary of Maximal Local Skin Reactions Post-Baseline for Picato (Ingenol Mebutate) ®

| Local Skin Responses | Grade | Pep005 Gel 0.015%[a] N = 274 | KX-01[b] (5-day) N = 84 | KX-01[b] (3-day) N = 84 |
|---|---|---|---|---|
| Erythema | 0 | 1 (<1%) | 15 (18%) | 30 (36%) |
|  | 1 | 25 (9%) | 16 (19%) | 22 (26%) |
|  | 2 | 56 (20%) | 35 (42%) | 26 (31%) |
|  | 3 | 125 (46%) | 17 (20%) | 6 (7%) |
|  | 4 | 66 (24%) | 1 (1%) | 0 (0%) |
| Flaking/ Scaling | 0 | 7 (3%) | 33 (39%) | 39 (46%) |
|  | 1 | 52 (19%) | 10 (12%) | 18 (21%) |
|  | 2 | 91 (33%) | 24 (29%) | 19 (23%) |
|  | 3 | 98 (36%) | 16 (19%) | 8 (10%) |
|  | 4 | 25 (9%) | 1 (1%) | 0 (0%) |
| Crusting | 0 | 44 (16%) | 51 (61%) | 58 (69%) |
|  | 1 | 85 (31%) | 25 (30%) | 16 (19%) |
|  | 2 | 64 (23%) | 8 (10%) | 9 (11%) |
|  | 3 | 64 (23%) | 0 (0%) | 1 (1%) |
|  | 4 | 16 (6%) | 0 (0%) | 0 (0%) |
| Swelling | 0 | 56 (20%) | 66 (79%) | 76 (90%) |
|  | 1 | 88 (32%) | 16 (19%) | 8 (10%) |
|  | 2 | 67 (25%) | 1 (1%) | 0 (0%) |
|  | 3 | 48 (18%) | 1 (1%) | 0 (0%) |
|  | 4 | 14 (5%) | 0 (0%) | 0 (0%) |
| Vesiculation/ Pustulation | 0 | 119 (43%) | 80 (95%) | 83 (99%) |
|  | 1 | 36 (13%) | 4 (5%) | 0 (0%) |
|  | 2 | 53 (19%) | 0 (0%) | 1 (1%) |
|  | 3 | 50 (18%) | 0 (0%) | 0 (0%) |
|  | 4 | 15 (6%) | 0 (0%) | 0 (0%) |
| Erosion/ Ulceration | 0 | 186 (68%) | 71 (85%) | 79 (94%) |
|  | 1 | 55 (20%) | 12 (14%) | 5 (6%) |
|  | 2 | 26 (10%) | 1 (1%) | 0 (0%) |
|  | 3 | 5 (2%) | 0 (0%) | 0 (0%) |
|  | 4 | 1 (<1%) | 0 (0%) | 0 (0%) |

[a]Source: NDA 202833; Statistical Review and Evaluation Pep005 (Ingenol Mebutate) gel, 0.015%; Table 9.
[b]Values are number of subjects in the Evaluable Set, categorized per their maximal post-baseline LSR grade.
Percentages are based on the number of subjects.

Example 3—Summary of PK Results from Studies in Examples 1 and 2

KX-01 was tested in adult subjects with actinic keratosis of the dorsal forearm (Example 1) and actinic keratosis on the face or scalp (Examples 2a and 2b). In Example 1, the plasma pharmacokinetics (PK) of KX-01 following topical administration was evaluated by collection of plasma on days 1 and 3 of the 3-day regimens and on days 1 and 5 of the 5-day regimens (Table 12). In Examples 2a and 2b, plasma samples were collected on days 1 and 5 of Cohort 1 (Table 13). Plasma samples at similar time points were collected on days 1 and 3 of Cohort 2. KX-01 was measured in human plasma using a validated LC-MS/MS assay with a lower limit of quantification (LLOQ) of 0.1 ng/mL.

TABLE 12

Example 1 - Treatment Regimens and PK Collection Times

| Cohort | Amount of KX-01 | Dosing Regimen | PK Collection Time (hr) |
|---|---|---|---|
| 1 | 0.5 mg over 25 cm$^2$ | Once daily for 3 days | Day 1: predose, 0.5, 1, 2, 4, 6, 8 and 12 postdose<br>Day 2: predose (24 postdose Day 1)<br>Day 3: pre-dose, 0.5, 1, 2, 4, 6, 8, 24, 48 and 120 postdose |
| 2 | 2 mg over 100 cm$^2$ | Once daily for 3 days | Day 1: predose, 0.5, 1, 2, 4, 6, 8, 12 postdose<br>Day 2: predose (24 hours postdose Day 1)<br>Day 3: pre-dose, 0.5, 1, 2, 4, 6, 8, 24, 48 and 120 postdose |
| 3 | 0.5 mg over 25 cm$^2$ | Once daily for 5 days | Day 1: predose, 0.5, 1, 2, 4, 6 postdose<br>Day 2: predose (24 hours postdose Day 1)<br>Day 5: predose, 0.5, 1, 2, 4, 6 and 72 postdose |
| 4 | 2 mg over 100 cm$^2$ | Once daily for 5 days | Day 1: predose, 0.5, 1, 2, 4, 6 postdose<br>Day 2: predose (24 hours postdose Day 1)<br>Day 5: predose, 0.5, 1, 2, 4, 6 and 72 postdose |

TABLE 13

Examples 2a and 2b - Treatment Regimens and PK Collection Times

| Cohort | Amount of KX-01 | Dosing Regimen | PK Collection Times (hr) |
|---|---|---|---|
| 1 | 0.5 mg over 25 cm$^2$ | Once daily for 5 days | Day 1: pre-dose, 0.5, 1 and 4 postdose<br>Day 5: pre-dose, 0.5, 1 and 4 postdose |
| 2 | 0.5 mg over 25 cm$^2$ | Once daily for 3 days | Day 1: pre-dose, 0.5, 1 and 4 postdose<br>Day 3: pre-dose, 0.5, 1 and 4 postdose |

Examination of PK data across these studies suggests that some of the plasma concentration data may be spurious. 75% of the concentrations in both studies are below the level of quantification (BLQ).

In study KX01-AK-002, PK data are available on 84 subjects in Cohort 1 treated once daily for 5 days, and 84 subjects in Cohort 2 treated once daily for 3 days, with 0.5 mg KX-01 over a 25 cm$^2$ dosing area on the face or scalp. Out of a total of 336 plasma samples analyzed from these 84 subjects following 1 day of treatment, 15 samples (~4%) were above the limit of quantification. Prior to the dose administered on Day 5 and 8 of 84 (~9%) subjects had quantifiable concentrations of KX-01. On Day 5 of dosing, measurable plasma concentrations were detected in 42 out of 84 subjects at 4 hours post-dose. All measurable plasma concentrations were below 0.7 ng/mL except for three aberrant samples.

Two of the three aberrant PK samples had observed plasma concentrations of 44 and 23 ng/mL occurring at 1 and 0.5 hours post-dose in two different subjects on Day 5. These primary PK samples were re-analyzed with comparable results. Analysis of the back-up PK samples resulted in concentrations of 0.351 ng/mL and BLQ, respectively. These results are more consistent with the KX-01 plasma concentration from the other 82 subjects and the other samples obtained from these subjects. One PK sample from a subject had an apparent plasma concentration above 12,500 ng/mL but the back-up sample had a plasma concentration of 30 ng/mL. The most likely cause of these aberrant results is cross contamination and the results do not represent real KX-01 plasma concentrations. All sites in study KX01-AK-002 have been retrained on the proper collection, handling and storage of PK samples.

In summary, the PK results of these studies showed that after 5 consecutive days of topical treatment with KX-01, low systemic exposure (less than 1 ng/mL) and limited drug accumulation was observed.

Example 4—KX-01 Phase 3 Study

A Phase 3, double-blind, vehicle-controlled, randomized, parallel group, multicenter, efficacy and safety study of KX2-391 in adult subjects with AK on the face or scalp will be conducted at approximately 25 sites in the United States, in order to study the following:
- the efficacy of topical administration of KX-01 daily for 5 consecutive days compared to vehicle control in terms of 100% clearance at Day 57 in the treatment of adults with actinic keratosis (AK), when applied to a contiguous area of 25 cm$^2$ on the face or scalp
- the safety of topical KX-01 daily for 5 consecutive days in terms of local skin reactions (LSRs) and other safety evaluations such as adverse events (AEs) and laboratory assessments
- the rates of partial responders defined as at least 75% clearance of AK lesions in the treatment area on the face or scalp at Day 57 between the KX-01-treated group and vehicle-treated group Topical treatment with KX-daily for 5 consecutive days will demonstrate a greater complete clearance (defined as 100% clearance of clinically typical and visible AK lesions at Day 57) than vehicle daily for 5 consecutive days in adults with actinic keratosis on the face or scalp.

Enrollment will be controlled so that approximately two thirds of subjects enrolled will be treated on the face and approximately one third of subjects enrolled will be treated on the scalp. Eligible subjects will be randomized centrally to treatment in a 1:1 (KX-01 or vehicle) ratio in each treatment area subgroup. That is to say, in either the face or scalp-treated subject subgroup, half of the subjects will receive the active study treatment randomly and the other half will receive vehicle control randomly.

The treatment area will be marked with indelible marker on Day 1 at the investigational sites. Subjects will be provided with daily single-dose units to be administered at home for 5 consecutive days. Subjects in both groups will be instructed to wash their hands and the treatment area, then dry the treatment area before application of KX-01. A small amount of KX-01 is to be applied to the fingertip and rubbed gently over the entire treatment area of 25 cm$^2$. Subjects will be instructed to wash their hands after applying the KX-01 and avoid washing the treatment area for at least 8 hours, and to avoid getting the KX-01 in the eyes. Subjects will return for follow-up for safety, LSR, and activity (AK lesion counts) evaluations at pre-specified time points until Day 57. All subjects who have unresolved LSRs, hypo- or hyperpigmentation, scarring, or treatment-related AEs at Day 57 will return for post-study follow-up every 7-28 days until resolution or deemed stabilized by the Investigators. Subjects who achieve 100% clearance of AK lesions in the treatment area at Day 57 will be invited to enroll in an extension protocol to determine recurrence rate and safety for up to 12 months.

A sufficient number of subjects will be screened to randomize approximately 300 subjects. At each site, a minimum of 10 subjects and a maximum of 20 subjects will be randomized.

Each subject will be in the study for up to 85 days: screening up to 28 days prior to day 1, treatment for 5 consecutive days, and follow-up until day 57. Use of any non-study drug treatment for AK lesions on the treatment area is prohibited until Day 57.

Inclusion Criteria
1. Males and females≥18 years old
2. A treatment area on the face or scalp that:
   is a contiguous area measuring 25 cm$^2$
   contains 4 to 8 clinically typical, visible and discrete AK lesions
3. Subjects who in the judgment of the Investigator, are in good general health based on:
   medical history
   physical examination (PE) findings
   electrocardiogram (ECG), clinical chemistry, hematology, and urinalysis results
4. Females must be postmenopausal (>45 years of age with at least 12 months of amenorrhea), surgically sterile (by hysterectomy, bilateral oophorectomy, or tubal ligation); or, if of childbearing potential, must be using highly effective contraception for at least 30 days or 1 menstrual cycle, whichever is longer, prior to treatment with KX01 and must agree to continue to use highly effective contraception for at least 30 days following their last dose of KX01. Highly effective contraception includes oral hormonal contraceptives, hormonal contraceptive implant, injection or patch, intrauterine device or complete abstinence from sexual intercourse for 2 weeks before dosing and throughout the study.
5. Males who have not had a vasectomy must agree to use barrier contraception from Screening through 90 days after their last dose of KX-01.
6. All subjects must agree not to donate sperm or eggs or attempt conception from Screening through 90 days following their last dose of KX-01.
7. Females of childbearing potential must have a negative serum pregnancy test at Screening and a negative urine pregnancy test on Day 1 prior to administration of study treatment.
8. Willing to avoid direct sun or ultraviolet (UV) light exposure to the face or scalp
9. Able to comprehend and are willing to sign an informed consent form (ICF)

Exclusion Criteria
1. Clinically atypical and/or rapidly changing AK lesions on the treatment area, e.g., hypertrophic, hyperkeratotic, recalcitrant disease (had cryosurgery on two previous occasions) and/or cutaneous horn
2. Location of the treatment area:
   On any location other than the face or scalp
   Within 5 cm of an incompletely healed wound
   Within 5 cm of a suspected basal cell carcinoma (BCC) or squamous cell carcinoma (SCC)
3. Been previously treated with KX-01
4. Anticipated need for in-patient hospitalization or in-patient surgery
5. Treatment with 5-fluorouracil (5-FU), imiquimod, ingenol mebutate, diclofenac, photodynamic therapy, or other treatments for AK within 2 cm of the treatment area, within 8 weeks prior to the Screening visit
6. Use of the following therapies and/or medications within 2 weeks prior to the Screening visit:
   Cosmetic or therapeutic procedures (e.g., use of liquid nitrogen, surgical excision, curettage, dermabrasion, medium or greater depth chemical peel, laser resurfacing) within 2 cm of the selected treatment area
   Acid-containing therapeutic products (e.g., salicylic acid or fruit acids, such as alpha- and beta-hydroxyl acids and glycolic acids), topical retinoids, or light chemical peels within 2 cm of the selected treatment area
   Topical salves (non-medicated/non-irritant lotion and cream are acceptable) or topical steroids within 2 cm of the selected treatment area; artificial tanners within 5 cm of the selected treatment area
7. Use of the following therapies and/or medications within 4 weeks prior to the Screening visit:
   Treatment with immunomodulators (e.g., azathioprine), cytotoxic drugs (e.g., cyclophosphamide, vinblastine, chlorambucil, methotrexate) or interferons/interferon inducers
   Treatment with systemic medications that suppress the immune system (e.g., cyclosporine, prednisone, methotrexate, alefacept, infliximab)
   Treatment/therapy with UVA or UVB
8. Use of systemic retinoids (e.g., isotretinoin, acitretin, bexarotene) within 6 months prior to the Screening visit
9. A history of sensitivity and/or allergy to any of the ingredients in the study medication
10. A skin disease (e.g., atopic dermatitis, psoriasis, eczema) or condition (e.g., scarring, open wounds) that, in the opinion of the Investigator, might interfere with the study conduct or evaluations, or which exposes the subject to unacceptable risk by study participation
11. Other significant uncontrolled or unstable medical diseases or conditions that, in the opinion of the Investigator, would expose the subject to unacceptable risk by study participation
12. Females who are pregnant or nursing
13. Participated in an investigational drug trial during which an investigational study medication was administered within 30 days or 5 half-lives of the investigational product, whichever is longer, before dosing Activity Assessments The Investigator or designee will perform a count of AK lesions in the treatment area for all subjects at Screening and on days 1 (Baseline), 8, 15, 29, and 57.

Safety Assessments

Safety will be assessed on days 1 (Baseline), 6, 8, 15, 29, and 57 by recording LSRs, AEs, and serious adverse events (SAEs).

Laboratory evaluation of hematology, biochemistry, and urinalysis values, measurement of weight, height, and vital signs, evaluation of ECGs, and PEs will be conducted at pre-specified time points.

Subjects will be queried for spontaneously reported AEs at each study visit, before assessment of LSRs. AEs will be reported separately from LSRs.

Other Assessments

The LSR assessment is the Investigator's (or trained designee's) assessment of the following signs on the treatment area: erythema, flaking/scaling, crusting, swelling, vesiculation/pustulation, and erosion/ulceration. These signs will be assessed using a grading scale ranging from 0=absent, 1=mild (slightly, barely perceptible), 2=moderate (distinct presence), and 3=severe (marked, intense).

In addition to LSRs, hypo- and hyper-pigmentation and scarring on the treatment area will be assessed as being present or absent. Application site reactions not classified as LSRs (e.g., pruritus, pain, infection) will be reported as adverse events. Investigators will be trained in the use of this LSR scale using representative photographs. Standardized photography will be performed on Day 1 prior to dosing, and on days 6, 8, 15, 29, and 57.

The primary efficacy endpoint is the complete clearance rate of AK lesions, defined as the proportion of subjects at Day 57 with no clinically visible AK lesions in the treatment area. The secondary efficacy endpoint is partial clearance rate of AK lesions defined as the proportion of subjects at Day 57 with a 75% or greater reduction in the number of AK lesions identified at Day 1 (Baseline) in the treatment area. Reduction in AK lesion counts during Days 1-57 will also be examined.

Safety endpoints includes evaluation of LSRs, pigmentation and scarring, AEs, SAEs, events of special interests, and clinical laboratory data; the results of other safety assessments (vital signs, PEs, ECGs) will also be evaluated.

The patient populations includes (1) Intent-To-Treat (ITT)/Safety Population: all randomized subjects who have received at least one day of treatment and returned for a follow-up visit and (2) Per-Protocol (PP)/Evaluable Population: all randomized subjects who have received at least 4 of the 5 doses, conformed to the protocol as to entry criteria, did not receive concomitant medications that can affect efficacy, and returned for the final visit at Day 57. This is the primary efficacy population.

The primary efficacy endpoint, complete clearance rate, will be compared based on a Cochran-Mantel-Haenszel (CMH) method controlling for treatment areas (face or scalp) between treatment groups. In addition, complete clearance rate comparison between treatment groups will be performed in the face and scalp-treated subgroups independently. Partial clearance rate will be analyzed in the same way as the primary efficacy endpoint (complete clearance rate).

To indicate concordance with the overall results, complete clearance rate will also be tabulated and displayed graphically as well in such subgroups as gender, age (<65 or ≥65 years), study site, baseline lesion count (4, 5, 6 or 7, 8), skin type (Fitzpatrick I/II or III/IV/V/VI). Outliers will be clinically explained in the clinical study report.

The number of AK lesions at Baseline, Day 57, and other visits and changes from baseline in the number of AK lesions at each visit will be summarized using descriptive statistics (i.e., mean, standard deviation, median, minimum and maximum), and then contrasted for each treatment group.

Safety analyses will be performed in the Safety Population.

Treatment-emergent AEs (TEAEs) are defined as either those AEs with an onset after dosing or those pre-existing AEs that worsen after dosing. For AEs, verbatim terms on the case report form/electronic case report form (CRF/eCRF) will be mapped to preferred terms (PTs) and system organ classes (SOCs) using the Medical Dictionary for Regulatory Activities (MedDRA; v 16.0 or higher). Subject incidence of AEs will be displayed by SOC. The incidence of TEAEs will be summarized by treatment group. TEAEs will also be summarized by severity, relationship to study treatment, and treatment group. Subject incidence of SAEs will also be displayed by treatment group. Laboratory parameters will be summarized using descriptive statistics at baseline and at each subsequent timepoint by treatment group. Changes from baseline will also be summarized by treatment group. In addition, shift tables (i.e., low-normal-high at baseline versus low-normal-high at follow-up in a 3-by-3 contingency table) will be provided to assess changes in laboratory values from baseline to follow-up in each treatment group. Local skin reactions, pigmentation, and scarring as reported by the Investigator, will be displayed and summarized by visit and treatment group for all subjects. Events of special interest will be summarized.

Example 5—KX-01 Phase 3 Extension Study
Protocol Synopsis (Recurrence Follow Up Protocol)

A 12-month prospective, longitudinal, follow-up study of complete responders from two Phase 3 studies of KX-01 administered topically in adult subjects with AK on the Face or Scalp will be conducted at approximately 25 sites in the United States, in order to determine the recurrence of actinic keratosis (AK) in the treatment area of subjects who had complete clearance at Day 57 in the Phase 3 studies of KX-01 and to study adverse events (AEs) in the treatment area.

Eligibility Criteria
1. Complete clearance defined as 100% clearance of AK lesions in the treatment area on Day 57 in subjects from the two Phase 3 studies
2. Willing to avoid direct sun or ultraviolet (UV) light exposure to the face or scalp
3. Able to comprehend and are willing to comply with study procedures and sign an informed consent form (ICF)

No subject will be re-treated with the study drug. Subjects will be prohibited from receiving field treatment or treatment that may mask the incidence of AK lesion recurrence (e.g., topical ingenol mebutate, 5-fluorouracil [5-FU], diclofenac, imiquimod) inside or within 2 cm of the treatment area at any time during the study. Isolated lesion treatment, such as cryotherapy or biopsy, will be allowed for treatment of AK lesions emerging in the selected treatment area. Clinic visits will occur at months 3, 6, 9, and 12 after the day 57 visit of the feeder Phase 3 studies. The number of AK lesions in the treatment area will be counted at each visit. If a subject receives lesion-specific treatment (i.e., cryotherapy or biopsy) for a lesion that appears in the treatment area, the treated lesion will be considered a recurrence. Information regarding intercurrent disorders, therapeutics that may result in immunosuppression, and treatment with agents known to alter AK will be collected. Adverse events and serious adverse events (SAEs), including skin cancers (basal cell carcinoma [BCC]/squamous cell carcinoma [SCC]/melanoma) in the treatment area or within 5 cm of the treatment area border will be reported. Other AEs and SAEs will be reported if they are considered by the Investigator to be related to study treatment. Standard photography will be performed at all visits.

For efficacy, the recurrence of AK lesion will be evaluated, which is defined as any identified AK lesion in the selected treatment area during the 12-month follow-up period for subjects who achieved complete clearance at the day 57 visit of the Phase 3 studies, regardless of the treatments they received previously. If a subject receives lesion-specific treatment (i.e., cryotherapy or biopsy) for a lesion that appears in the treatment area, the treated lesion is considered a recurrence.

For safety, AEs in the selected treatment area will be evaluated during the 12-month follow-up period. Other AEs which are reported by the investigators as being treatment-related will be evaluated as well.

The analysis population includes all subjects who achieved complete clearance at the day 57 visit of the feeder Phase 3 studies, regardless of which treatments they received previously. Both efficacy and safety analyses will be performed based on this population.

Analysis results by previous treatment groups (active treatment vs vehicle control) will be mainly contrasted by tabulations and graphs. The Kaplan-Meier method-based recurrence rate with a 95% confidence interval (CI) will be estimated at scheduled post-baseline visits (3, 6, 9, and 12 months) by previous treatment. The time when lesion(s) is/are observed will be imputed to the corresponding target study day (e.g., 91 days for the 3-month visit). The Kaplan-Meier method-based recurrence rate with a 95% confidence interval (CI) will be estimated at scheduled post-baseline visits (3, 6, 9, and 12 months) by previous treatment. The time when lesion(s) is/are observed will be imputed to the corresponding target study day (e.g., 91 days for the 3-month visit).

In addition, the Kaplan-Meier method-based median time to recurrence (i.e., appearance of a new or recurrent lesion in the treatment area) will be displayed graphically by previous treatment. The number of AK lesion counts in the treatment area will be summarized at each scheduled post-baseline visit by previous treatment. Furthermore, the number of lesions in the treatment area normalized by corresponding baseline lesion counts from the Phase 3 studies (expressed as percentages) will be summarized at each scheduled post-baseline visit by previous treatment.

For AEs that are collected in the treatment area, verbatim terms on the case report form/electronic case report form (CRF/eCRF) will be mapped to preferred terms (PTs) and system organ classes (SOCs) using the Medical Dictionary for Regulatory Activities (MedDRA; v 16.0 or higher). Subject incidence of AEs will be displayed by SOC and PT. The incidence of AEs will be summarized by previous treatment. Subject incidence of SAEs will be displayed by previous treatment. Adverse events that are reported by the Investigators as being treatment-related will be evaluated in the same way, but separately.

Example 6—Comparison of Skin Reaction with KX-01 Compared with Picato (Ingenol Mebutate)®, the Standard of Care Treatment of AK Initial data from the patients in the studies described herein (e.g., Example 1 and Examples 2a and 2b) demonstrate that the efficacy of KX-01 for clearing AK lesions may be similar to Picato (Ingenol Mebutate)®, the approved therapy for AK. Additionally, treatment with KX-01 results in fewer and less severe skin reactions in the subject, i.e., less skin toxicity, compared to Picato (Ingenol Mebutate)®.

Figure 3A:
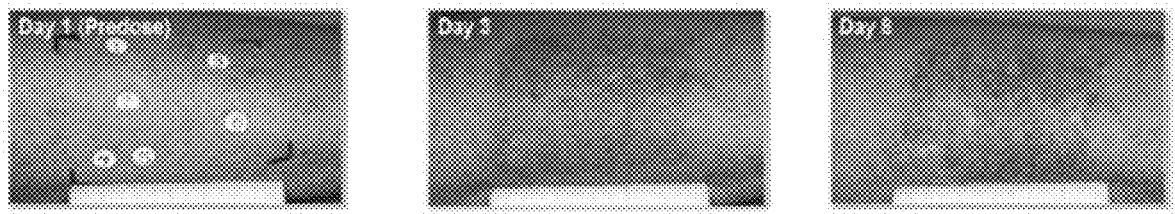
FIGS. 3A and 3B. Comparison of skin reactions on forearms in patients treated with Picato (Ingenol Mebutate)® (FIG. 3A) vs. KX-01 (FIG. 3B).
Figure 3B:
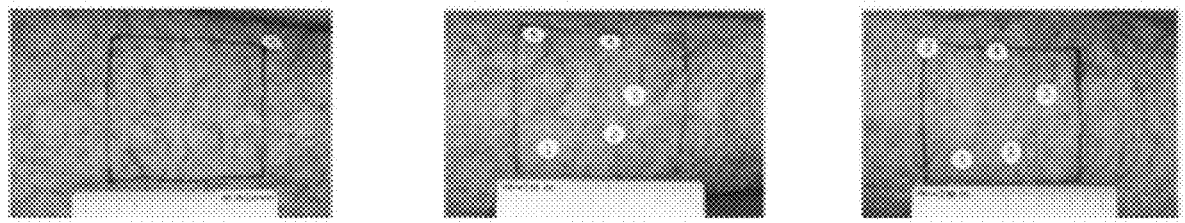

This is illustrated in FIGS. 3A and 3B, which demonstrate the skin reaction in the forearm of subject at day 3 and day 5 of treatment with Picato (Ingenol Mebutate)®, which shows severe skin reactions (FIG. 3A). Comparatively, the forearm of subject at day 3 and day 5 of treatment with KX-01, in a subject who had a 100% response to KX-01 topical treatment, exhibits minimal or no adverse skin reactions (FIG. 3B).

Figure 4A:
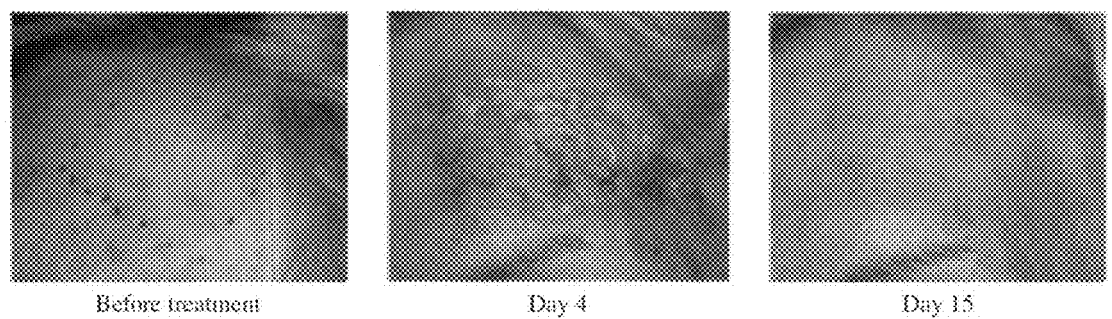
FIGS. 4A and 4B. Comparison of skin reactions on foreheads in patients treated with Picato (Ingenol Mebutate)® (FIG. 4A) vs. KX-01 (FIG. 4B).
Figure 4B:
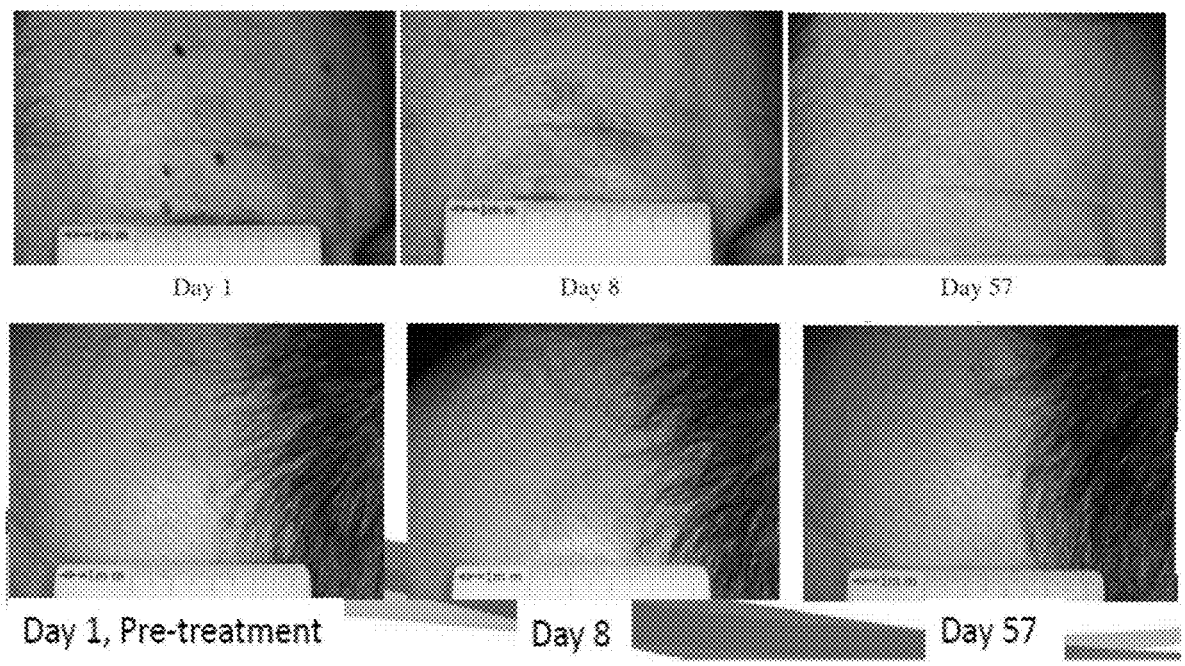

Similarly, FIGS. 4A and 4B illustrate the adverse skin reaction in the forehead of a subject at day 4 and day 15 of treatment with Picato (Ingenol Mebutate)®, which shows severe skin reactions (FIG. 4A). Comparatively, the forehead of a subject at day 8 and day 57 of treatment with KX-01, in a subject who had a 100% response to KX-01 topical treatment, also exhibits minimal or no adverse skin reactions (FIG. 4B).

The comparison in FIGS. 3A, 3B, 4A, and 4B illustrates the lack of skin toxicity observed in the treatment of AK with topically administered KX-01 compared to the approved therapy for AK. This is likely to be a significant consideration of clinicians and patients, and, to the extent that skin toxicity has been limiting to the market of current treatment options for subjects suffering from AK, KX-01 may significantly expand the market as a result of less skin toxicity.

EQUIVALENTS

The disclosure of the application can be embodied in other specific forms without departing from the spirit or essential characteristics thereof. The foregoing embodiments are therefore to be considered in all respects illustrative rather than limiting on the disclosure of the application described herein. Scope of the disclosure of the application is thus indicated by the appended claims rather than by the foregoing description, and all changes that come within the meaning and range of equivalency of the claims are intended to be embraced therein.

The invention claimed is:

1. A method of treating actinic keratosis comprising administering to a subject in need thereof a therapeutically effective amount of a compound of the following structure:

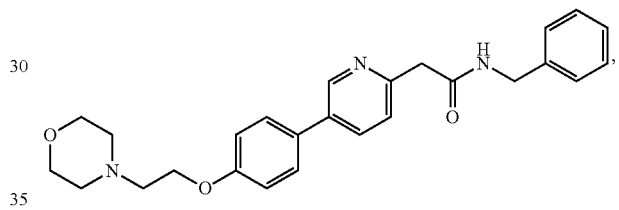

at a dose from about 0.02 mg/cm$^2$ to about 0.1 mg/cm$^2$.

2. The method of claim 1, wherein the compound is administered to an affected area of the subject at a dose from about 0.2 mg to about 5 mg.

3. The method of claim 1, wherein the compound is administered to an affected area of the subject at a dose of about 0.2 mg, about 0.3 mg, about 0.4 mg, about 0.5 mg, about 0.6 mg, about 0.7 mg, about 0.8 mg, about 0.9 mg, about 1 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3 mg, about 4 mg, or about 5 mg.

4. The method of claim 1, wherein the compound is administered to an affected area of the subject at a dose from about 0.025 mg/cm$^2$ to about 0.1 mg/cm$^2$.

5. The method of claim 1, wherein the compound is administered to an affected area of the subject at a dose of about 0.02 mg/cm$^2$, about 0.03 mg/cm$^2$, about 0.04 mg/cm$^2$, about 0.05 mg/cm$^2$, about 0.06 mg/cm$^2$, about 0.07 mg/cm$^2$, about 0.08 mg/cm$^2$, about 0.09 mg/cm$^2$, or about 0.1 mg/cm$^2$.

6. The method of claim 2, wherein the affected area is about 1 cm$^2$ to about 200 cm$^2$.

7. The method of claim 2, wherein the affected area is about 25 cm$^2$, about 30 cm$^2$, about 35 cm$^2$, about 40 cm$^2$, about 45 cm$^2$, about 50 cm$^2$, about 55 cm$^2$, about 60 cm$^2$, about 65 cm$^2$, about 70 cm$^2$, about 75 cm$^2$, about 80 cm$^2$, about 85 cm$^2$, about 90 cm$^2$, about 95 cm$^2$, or about 100 cm$^2$.

8. The method of claim 2, wherein the affected area is the skin.

9. The method of claim 1, wherein the compound is administered once a week, once every three days, once every two days, once a day, twice a day, three times a day, or four times a day.

10. The method of claim 1, wherein the compound is administered for 1, 2, 3, 4, 5, 6, 7, 8, 9, 10, 11, 12, 13, 14, 15, 16, 17, 18, 19, 20, or 21 days.

11. The method of claim 1, wherein the compound is administered for 1, 2, 3, 4, or 5 days.

12. The method of claim 1, wherein the compound is administered for 1, 2, 3, 4, 5, or 6 days per week.

13. The method of claim 1, wherein the compound is administered once or twice daily continuously for more than one day per week, followed by discontinuation of the administration for the rest of the week.

14. The method of claim 1, wherein the compound is administered once or twice daily every other day, every three days, every four days, every five days, every six days, or every seven days.

15. The method of claim 1, wherein the compound is administered once or twice daily for two days in a row every three days, every four days, every five days, every six days, or every seven days.

16. The method of claim 1, wherein the compound is administered once or twice daily for three days in a row every four days, every five days, every six days, or every seven days.

17. The method of claim 1, wherein the compound is administered once or twice daily for four days in a row every five days, every six days, or every seven days.

18. The method of claim 1, wherein the compound is administered until the actinic keratosis is fully treated.

19. The method of claim 1, wherein the compound is administered topically.

20. The method of claim 1, wherein the administration of the compound reduces the number and/or severity of, or the number of the subjects that have, local skin reactions or other adverse side effects in the subject compared to other treatments of actinic keratosis.

21. The method of claim 1, wherein the compound is administered once daily.

22. The method of claim 1, wherein the compound is administered for 3 days.

23. The method of claim 1, wherein the compound is administered for 5 days.

24. The method of claim 1, wherein the compound is administered at a dose of about 0.02 mg/cm$^2$ once daily for 3 days.

25. The method of claim 1, wherein the compound is administered at a dose of about 0.02 mg/cm$^2$ once daily for 5 days.

* * * * *